United States Patent
Tsubouchi et al.

(10) Patent No.: US 8,344,148 B2
(45) Date of Patent: Jan. 1, 2013

(54) EPOXY COMPOUND AND METHOD FOR MANUFACTURING THE SAME

(75) Inventors: Hidetsugu Tsubouchi, Osaka (JP); Yoshikazu Haraguchi, Osaka (JP); Satoshi Hayakawa, Osaka (JP); Naoto Utsumi, Osaka (JP); Shinichi Taira, Osaka (JP); Yoshihisa Tanada, Osaka (JP); Nobuhisa Fujita, Osaka (JP); Koichi Shinhama, Osaka (JP); Kimiyoshi Annaka, Osaka (JP); Takuya Furuta, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 298 days.

(21) Appl. No.: 12/599,214

(22) PCT Filed: May 7, 2008

(86) PCT No.: PCT/JP2008/058798
§ 371 (c)(1),
(2), (4) Date: Nov. 6, 2009

(87) PCT Pub. No.: WO2008/140090
PCT Pub. Date: Nov. 20, 2008

(65) Prior Publication Data
US 2010/0217005 A1    Aug. 26, 2010

(30) Foreign Application Priority Data
May 8, 2007 (JP) .................................. 2007-123097

(51) Int. Cl.
*C07D 211/46* (2006.01)
(52) U.S. Cl. .................................................... 546/199
(58) Field of Classification Search ................... 546/199
See application file for complete search history.

(56) References Cited

U.S. PATENT DOCUMENTS
7,262,212 B2 *   8/2007   Tsubouchi et al. ........... 514/375

FOREIGN PATENT DOCUMENTS
| WO | WO-2004/033463 A1 | 4/2004 |
| WO | WO-2004/035547 A1 | 4/2004 |
| WO | WO-2005/042542 A1 | 5/2005 |

OTHER PUBLICATIONS

Drabczyńska et al., "Tricyclic Oxazolo[2,3-*f*]Purinediones: Potency as Adenosine Receptor Ligands and Anticonvulsants", Bioorganic & Medicinal Chemistry vol. 12, No. 18, pp. 4895-4908, (2004).
Ren-Hua et al., "Reaction Between 8-Chlorotheophylline and Epoxides", Tetrahedron Letters, vol. 33, No. 42, pp. 6307-6308, (1992).
Nagarajan et al., "Nitroimidazoles XXI 2,3-Dithydro-6-Nitroimidazo [2,1-*b*] Oxazol With Antitubercular Activity", European Journal of Medical Chemistry, vol. 24, pp. 631-633, (1989).
Sehgal et al., "Potential Radiosensitizing Agents. 2. Synthesis and Biological Activity of Derivatives of Dinitroimidazole with Oxiranes", Journal of Medicinal Chemistry, vol. 24, No. 5, pp. 601-604, (1981).
International Search Report from the European Patent Office for International Application No. PCT/JP/2008/058798 (Sep. 1, 2008).

* cited by examiner

*Primary Examiner* — David K O'Dell
(74) *Attorney, Agent, or Firm* — Finnegan, Henderson, Farabow, Garrett & Dunner, L.L.P.

(57) ABSTRACT

The present invention provides a novel intermediate for manufacturing a 2,3-dihydroimidazo[2,1-b]oxazole compound with a high yield and a high purity, and a manufacturing method of the intermediate. The present invention provides an epoxy compound represented by the general formula (2): wherein, R1 represents hydrogen or a lower alkyl group; and R2 represents a piperidyl group represented by the general formula (A1): (wherein, R3 represents a phenoxy group having a halogen-substituted lower alkoxy group substituted on a phenyl group, and the like) and the like; and n represents an integer of 1 to 6, a manufacturing method of the epoxy compound, and a manufacturing method of an oxazole compound using the epoxy compound.

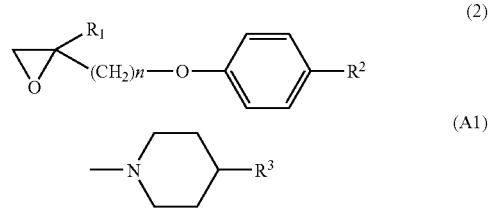

1 Claim, No Drawings

EPOXY COMPOUND AND METHOD FOR MANUFACTURING THE SAME

TECHNICAL FIELD

The present invention relates to an epoxy compound and a method for manufacturing the same.

BACKGROUND ART

A 2,3-dihydroimidazo[2,1-b]oxazole compound or salts thereof are useful compounds as an antitubercular agent (WO2004/033463, WO2004/035547 and WO2005/042542), the oxazole compound or salts thereof are represented by the general formula (1):

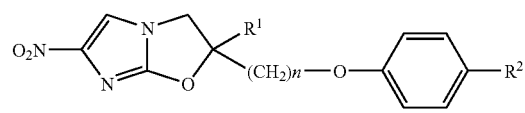

wherein $R^1$ represents hydrogen or a lower alkyl group;
$R^2$ represents a piperidyl group represented by the general formula (A1):

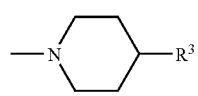

(wherein $R^3$ represents:
(A1a) a phenoxy group having a halogen-substituted lower alkoxy group(s) as a substituent(s) on a phenyl group,
(A1b) a phenoxy-substituted lower alkyl group having a halogen-substituted lower alkyl group(s) as a substituent(s) on a phenyl group,
(A1c) a phenyl-substituted lower alkoxy lower alkyl group having a halogen(s) as a substituent(s) on a phenyl group,
(A1d) a phenyl-substituted lower alkyl group having a halogen-substituted lower alkoxy group(s) as a substituent(s) on a phenyl group,
(A1e) an amino group having a phenyl group having a halogen-substituted lower alkoxy group(s) as a substituent(s) on a phenyl group, and a lower alkyl group, or
(A1f) a phenyl-substituted lower alkoxy group having a halogen-substituted lower alkoxy group(s) as a substituent(s) on a phenyl group), or a piperazyl group represented by the general formula (A2):

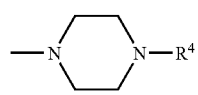

(wherein $R^4$ represents:
(A2a) a phenyl-substituted lower alkenyl group having a halogen-substituted lower alkoxy group(s) as a substituent(s) on a phenyl group, or
(A2b) a halogen-substituted phenyl group); and
n represents an integer of 1 to 6. These Patent Documents disclose, as a manufacturing method of the 2,3-dihydroimidazo[2,1-b]oxazole compound, for example, a method shown by the following Reaction Formula A:

Reaction Formula A

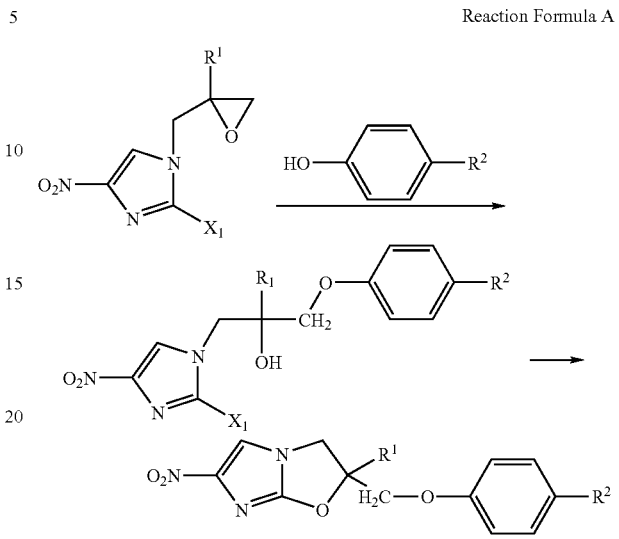

wherein $R^1$, $R^2$ and n are the same as in the above; and
$X^1$ represents a halogen atom or a nitro group.

The above-mentioned oxazole compound is an important compound as antitubercular agent, and the development of alternative methods for manufacturing industrially and profitably the compound is much desired.

It is an object of the present invention to provide a novel intermediate for manufacturing a 2,3-dihydroimidazo[2,1-b]oxazole compound represented by the general formula (1) in a high yield and a high purity, and a manufacturing method of the intermediate.

DISCLOSURE OF THE INVENTION

As a result of intensive studies on a manufacturing method of a 2,3-dihydroimidazo[2,1-b]oxazole compound represented by the above general formula (1), the present inventors have found that using an epoxy compound represented by the below general formula (2) as a starting raw material enables to manufacture a 2,3-dihydroimidazo[2,1-b]oxazole compound represented by the general formula (1), which is an active principle of an anti-tubercular agent in a high yield and with a high purity. This finding has led to the completion of the present invention.

The present invention provides an epoxy compound or salts thereof, shown in Item 1 and Item 2 below.

Item 1:

To provide an epoxy compound or salts thereof represented by the general formula (2):

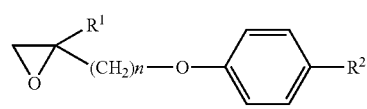

wherein $R^1$ represents hydrogen or a lower alkyl group;

$R^2$ represents a piperidyl group represented by the general formula (A1):

(wherein $R^3$ represents:
(A1a) a phenoxy group having a halogen-substituted lower alkoxy group(s) as a substituent(s) on a phenyl group,
(A1b) a phenoxy-substituted lower alkyl group having a halogen-substituted lower alkyl group(s) as a substituent(s) on a phenyl group,
(A1c) a phenyl-substituted lower alkoxy lower alkyl group having a halogen(s) as a substituent(s) on a phenyl group,
(A1d) a phenyl-substituted lower alkyl group having a halogen-substituted lower alkoxy group(s) as a substituent(s) on a phenyl group,
(A1e) an amino group having a phenyl group having a halogen-substituted lower alkoxy group(s) as a substituent(s) on a phenyl group, and a lower alkyl group, or
(A1f) a phenyl-substituted lower alkoxy group having a halogen-substituted lower alkoxy group(s) as a substituent(s) on a phenyl group), or a piperazyl group represented by the general formula (A2):

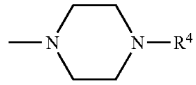

(wherein $R^4$ represents:
(A2a) a phenyl-substituted lower alkenyl group having a halogen-substituted lower alkoxy group(s) as a substituent(s) on a phenyl group, or
(A2b) a halogen-substituted phenyl group; and
n represents an integer of 1 to 6.
Item 2:
To provide an epoxy compound or salts thereof selected from the group consisting of:
1) (R)-1-[4-(2,3-epoxy-2-methylpropoxy)phenyl]-4-(4-trifluoromethoxyphenoxy)piperidine;
2) (R)-1-[4-(2,3-epoxypropoxy)phenyl]-4-(4-trifluoromethoxyphenoxy)piperidine;
3) (R)-1-[4-(2,3-epoxy-2-methylpropoxy)phenyl]-4-(4-trifluoromethylphenoxymethyl)piperidine;
4) (R)-1-[4-(2,3-epoxypropoxy)phenyl]-4-(4-trifluoromethyl-phenoxymethyl)piperidine;
5) (R)-1-[4-(2,3-epoxy-2-methylpropoxy)phenyl]-4-[3-(4-trifluoromethoxyphenyl)-2-propenyl]piperazine;
6) (R)-1-[4-(2,3-epoxypropoxy)phenyl]-4-[3-(4-trifluoromethoxyphenyl)-2-propenyl]piperazine;
7) (R)-4-(4-chlorobenzyloxymethyl)-1-[4-(2,3-epoxy-2-methylpropoxy)phenyl]piperidine;
8) (R)-4-(4-chlorobenzyloxymethyl)-1-[4-(2,3-epoxypropoxy)phenyl]piperidine;
9) (R)-1-[4-(2,3-epoxy-2-methylpropoxy)phenyl]-4-(4-trifluoromethoxybenzyl)piperidine;
10) (R)-1-[4-(2,3-epoxypropoxy)phenyl]-4-(4-trifluoromethoxybenzyl)piperidine;
11) (R)-1-[4-(2,3-epoxy-2-methylpropoxy)phenyl]-4-[N-methyl-N-(4-trifluoromethoxyphenyl)]aminopiperidine;
12) (R)-4-[N-methyl-N-(4-trifluoromethoxyphenyl)]amino-1-[4-(2,3-epoxypropoxy)phenyl]piperidine;
13) (R)-1-(4-chlorophenyl)-4-[4-(2,3-epoxy-2-methylpropoxy)phenyl]piperazine;
14) (R)-1-(4-chlorophenyl)-4-[4-(2,3-epoxypropoxy)phenyl]piperazine;
15) (R)-1-[4-(2,3-epoxy-2-methylpropoxy)phenyl]-4-(4-trifluoromethoxybenzyloxy)piperidine; and
16) (R)-1-(4-(oxiranylmethoxy)phenyl)-4-(4-(trifluoromethoxy)benzyloxy)piperidine.

The present invention further provides a manufacturing method of an epoxy compound or salts thereof, shown in Item 3 below.
Item 3:
To provide a method for manufacturing an epoxy compound or salts thereof represented by the general formula (2):

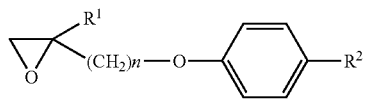

wherein $R^1$, $R^2$ and n are the same as the above, by reacting a compound or salts thereof represented by the general formula (3):

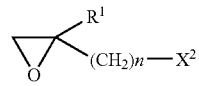

wherein $R^1$ and n are the same as the above; and
$X^2$ represents a halogen or a group(s) causing a substitution reaction similar to that of a halogen with a compound or salts thereof represented by the general formula (4):

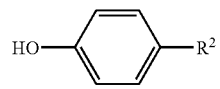

wherein $R^2$ is the same as the above.

The present invention further provides a manufacturing method of an oxazole compound or salts thereof shown in Item 4 below.
Item 4:
To provide a method for manufacturing an oxazole compound or salts thereof represented by the general formula (1):

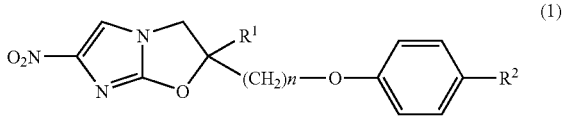

wherein $R^1$, $R^2$ and n are the same as the above, by reacting a compound or salts thereof represented by the general formula (5):

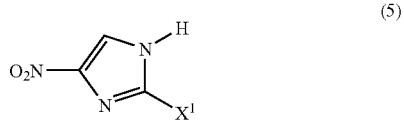

wherein $X^1$ represents a halogen atom, with an epoxy compound or salts thereof represented by the general formula (2):

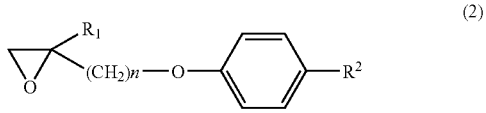

wherein $R^1$, $R^2$ and n are the same as the above.

An epoxy compound or salts thereof of the general formula (2) according to the present invention is a novel compound which is not described in any documents.

An epoxy compound or salts thereof of the general formula (2) according to the present invention are useful as an intermediate for manufacturing an oxazole compound or salts thereof represented by the general formula (1), which is important as a synthesized intermediate for medicinals and agrichemicals, especially as an anti-tubercular agent.

An epoxy compound represented by the above general formula (2) is preferably a compound or salts thereof selected from the group consisting of:

1) (R)-1-[(4-(2,3-epoxy-2-methylpropoxy)phenyl]-4-(4-trifluoromethoxyphenoxy)piperidine;
2) (R)-1-[4-(2,3-epoxypropoxy)phenyl]-4-(4-trifluoromethoxyphenoxy)piperidine;
3) (R)-1-[4-(2,3-epoxy-2-methylpropoxy)phenyl]-4-(4-trifluoromethylphenoxymethyl)piperidine;
4) (R)-1-[4-(2,3-epoxypropoxy)phenyl]-4-(4-trifluoromethylphenoxymethyl)piperidine;
5) (R)-1-[4-(2,3-epoxy-2-methylpropoxy)phenyl]-4-[3-(4-trifluoromethoxyphenyl)-2-propenyl]piperazine;
6) (R)-1-[4-(2,3-epoxypropoxy)phenyl]-4-[3-(4-trifluoromethoxyphenyl)-2-propenyl]piperazine;
7) (R)-4-(4-chlorobenzyloxymethyl)-1-[4-(2,3-epoxy-2-methylpropoxy)phenyl]piperidine;
8) (R)-4-(4-chlorobenzyloxymethyl)-1-[4-(2,3-epoxypropoxy)phenyl]piperidine;
9) (R)-1-[4-(2,3-epoxy-2-methylpropoxy)phenyl]-4-(4-trifluoromethoxybenzyl)piperidine;
10) (R)-1-[4-(2,3-epoxypropoxy)phenyl]-4-(4-trifluoromethoxybenzyl)piperidine;
11) (R)-1-[4-(2,3-epoxy-2-methylpropoxy)phenyl]-4-[N-methyl-N-(4-trifluoromethoxyphenyl)]aminopiperidine;
12) (R)-4-[N-methyl-N-(4-trifluoromethoxyphenyl)]amino-1-[4-(2,3-epoxypropoxy)phenyl]piperidine;
13) (R)-1-(4-chlorophenyl)-4-[4-(2,3-epoxy-2-methylpropoxy)phenyl]piperazine;
14) (R)-1-(4-chlorophenyl)-4-[4-(2,3-epoxypropoxy)phenyl]piperazine;
15) (R)-1-[4-(2,3-epoxy-2-methylpropoxy)phenyl]-4-(4-trifluoromethoxybenzyloxy)piperidine; and
16) (R)-1-(4-(oxiranylmethoxy)phenyl)-4-(4-(trifluoromethoxy)benzyloxy)piperidine.

Each group described in the present specification is specifically as follows.

The halogen atoms include a fluorine atom, chlorine atom, bromine atom and iodine atom.

The lower alkoxy groups include, for example, linear or branched alkoxy groups having 1 to 6 carbon atoms (preferably 1 to 4 carbon atoms). More specifically, they include methoxy, ethoxy, n-propoxy, isopropoxy, n-butoxy, isobutoxy, tert-butoxy, sec-butoxy, n-pentyloxy, 1-ethylpropoxy, isopentyloxy, neopentyloxy, n-hexyloxy, 1,2,2-trimethylpropoxy, 3,3-dimethylbutoxy, 2-ethylbutoxy, isohexyloxy and 3-methylpentyloxy groups.

The halogen-substituted lower alkoxy groups include the lower alkoxy groups as mentioned above having 1 to 7, preferably 1 to 3, halogen atoms as a substituent(s). More specifically, they include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentyloxy, 5-chloropentyloxy, 6,6,6-trifluorohexyloxy and 6-chlorohexyloxy groups.

The phenoxy groups having a halogen-substituted lower alkoxy group on a phenyl group as a substituent(s) include, for example, phenoxy groups having 1 to 3 (preferably 1) the halogen-substituted lower alkoxy groups as mentioned above on a phenyl group as a substituent(s).

The lower alkyl groups include linear or branched alkyl groups having 1 to 6 carbon atoms (preferably 1 to 4 carbon atoms). More specifically, they include methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl and 3-methylpentyl groups.

The halogen-substituted lower alkyl groups include the lower alkyl groups as mentioned above having 1 to 7, preferably 1 to 3, halogen atoms as a substituent(s). More specifically, they include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl and 6-chlorohexyl groups.

The phenoxy-substituted lower alkyl groups are exemplified by the lower alkyl groups as mentioned above having one phenoxy group as a substituent. More specifically, they include phenoxymethyl, 2-phenoxyethyl, 1-phenoxyethyl, 2-phenoxyethyl, 2-phenoxy-1-methylethyl, 2-phenoxy-1-ethylethyl, 3-phenoxypropyl and 4-phenoxybutyl groups.

The phenoxy-substituted lower alkyl groups having a halogen-substituted lower alkyl group(s) as a substituent(s) on a phenyl group include, for example, the phenoxy-substituted lower alkyl groups as mentioned above having 1 to 3 (preferably 1) halogen-substituted lower alkyl group(s) as mentioned above as a substituent(s) on a phenyl group.

The lower alkoxy lower alkyl groups are exemplified by the lower alkyl groups as mentioned above having one lower alkoxy group as mentioned above as a substituent. More specifically, they include methoxymethyl, 2-methoxyethyl, 1-ethoxyethyl, 2-ethoxyethyl, 2-isobutoxyethyl, 2,2-dimethoxyethyl, 2-methoxy-1-methylethyl, 2-methoxy-1-ethylethyl, 3-methoxypropyl, 3-ethoxypropyl, 3-isobutoxypropyl, 3-n-butoxypropyl, 4-n-propoxybutyl, 1-methyl-3-isobutoxypropyl, 1,1-dimethyl-2-n-pentyloxyethyl, 5-n- hexyloxypentyl, 6-methoxyhexyl, 1-ethoxyisopropyl and 2-methyl-3-methoxypropyl groups.

The phenyl-substituted lower alkoxy lower alkyl groups are exemplified by the lower alkoxy lower alkyl groups as mentioned above having one phenyl group as a substituent on a lower alkoxy group. More specifically, they include benzyloxymethyl, (2-phenylethoxy)methyl, (1-phenylethoxy)methyl, 3-(3-phenylpropoxy)propyl, 4-(4-phenylbutoxy)butyl, 5-(5-phenylpentyloxy)pentyl, 6-(6-phenylhexyloxy)hexyl, 1,1-dimethyl-(2-phenylethoxy)ethyl, 2-methyl-3-(3-phenylpropoxy)propyl, 2-benzyloxyethyl, 1-benzyloxyethyl, 3-benzyloxypropyl, 4-benzyloxybutyl, 5-benzyloxypentyl and 6-benzyloxyhexyl groups.

The phenyl-substituted lower alkoxy lower alkyl groups having a halogen(s) as a substituent(s) on a phenyl group include, for example, the phenyl-substituted lower alkoxy lower alkyl groups as mentioned above having 1 to 7, more preferably 1 to 3, the halogen atom(s) as a substituent(s) on a phenyl group.

The phenyl-substituted lower alkyl groups are exemplified by the lower alkyl groups as mentioned above having one phenyl group as a substituent. More specifically, they include benzyl, 1-phenylethyl, 2-phenylethyl, 1-methyl-1-phenylethyl, 1,1-dimethyl-2-phenylethyl, 1,1-dimethyl-3-phenylpropyl, 3-phenylpropyl and 4-phenylbutyl groups.

The phenyl-substituted lower alkyl groups having a halogen-substituted lower alkoxy group(s) as a substituent(s) on a phenyl group include, for example, the phenyl-substituted lower alkyl groups as mentioned above having 1 to 3 (preferably 1) halogen-substituted lower alkoxy groups as mentioned above as a substituent(s) on a phenyl group.

The phenyl groups having a halogen-substituted lower alkoxy group(s) as a substituent(s) on a phenyl group include, for example, phenyl groups having 1 to 3 (preferably 1) halogen-substituted lower alkoxy group(s) as a substituent(s) on a phenyl group.

The amino groups having a phenyl group having a halogen-substituted lower alkoxy group(s) as a substituent(s) on a phenyl group and a lower alkyl group as a substituent include, for example, amino groups having, on an amino group, one phenyl group as mentioned above having a halogen-substituted lower alkoxy group(s) as a substituent(s) on a phenyl group and one lower alkyl group.

The phenyl-substituted lower alkoxy groups are exemplified by the lower alkyl groups as mentioned above having one phenyl group as a substituent. More specifically, they include benzyloxy, 1-phenylethoxy, 2-phenylethoxy, 1-methyl-1-phenylethoxy, 1,1-dimethyl-2-phenylethoxy, 1,1-dimethyl-3-phenylpropoxy, 3-phenylpropoxy and 4-phenylbutoxy groups.

The phenyl-substituted lower alkoxy groups having a halogen-substituted lower alkoxy group(s) as a substituent(s) on a phenyl group include, for example, the phenyl-substituted lower alkoxy groups having 1 to 3 (preferably 1) halogen-substituted lower alkoxy group(s) as mentioned above as a substituent(s) on a phenyl group.

The lower alkenyl groups include linear or branched alkenyl groups having 1 to 3 double bond(s) and having 2 to 6 carbon atoms, and include both the trans form and cis form. More specifically, they include vinyl, 1-propenyl, 2-propenyl, 1-methyl-1-propenyl, 2-methyl-1-propenyl, 2-methyl-2-propenyl, 2-propenyl, 2-butenyl, 1-butenyl, 3-butenyl, 2-pentenyl and 1-pentenyl groups.

The phenyl-substituted lower alkenyl groups are exemplified by the lower alkenyl groups as mentioned above having one phenyl group as a substituent. More specifically, they include 2-phenylvinyl, 3-phenyl-1-propenyl, 3-phenyl-2-propenyl, 3-phenyl-1-methyl-1-propenyl, 3-phenyl-2-methyl-1-propenyl, 3-phenyl-2-methyl-2-propenyl, 4-phenyl-2-butenyl, 4-phenyl-1-butenyl, 4-phenyl-3-butenyl, 5-phenyl-2-pentenyl and 5-phenyl-1-pentenyl groups.

The phenyl-substituted lower alkenyl groups having a halogen-substituted lower alkoxy group(s) as a substituent(s) on a phenyl group include, for example, the phenyl-substituted lower alkenyl groups as mentioned above having 1 to 3 (preferably 1) halogen-substituted lower alkoxy group(s) as mentioned above as a substituent(s) on a phenyl group.

The halogen-substituted phenyl groups include, for example, the phenyl group(s) as mentioned above having 1 to 7, preferably 1 to 3, halogen atom(s) as a substituent(s).

The manufacturing method of an epoxy compound of the general formula (2) according to the present invention will be described hereinafter.

[Reaction Formula-1]

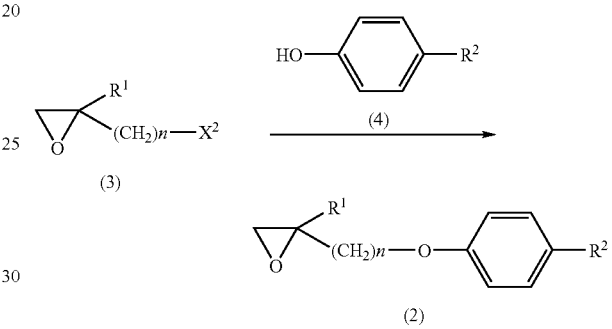

[wherein, $R^1$, $X^2$ and n are the same as the above.]

The groups causing the substitution reaction similar to that of a halogen atom represented by $X^2$ are exemplified by lower alkanesulfonyloxy groups, arylsulfonyloxy groups and aralkylsulfonyloxy groups.

The lower alkanesulfonyloxy groups are specifically exemplified by linear or branched alkanesulfonyloxy groups having 1 to 6 carbon atoms, such as methanesulfonyloxy, ethanesulfonyloxy, n-propanesulfonyloxy, isopropanesulfonyloxy, n-butanesulfonyloxy, tert-butanesulfonyloxy, n-pentanesulfonyloxy and n-hexanesulfonyloxy groups.

The arylsulfonyloxy groups include, for example, phenylsulfonyloxy and naphthylsulfonyloxy groups which may have 1 to 3 groups selected from the group consisting of linear or branched alkyl groups having 1 to 6 carbon atoms, linear or branched alkoxy groups having 1 to 6 carbon atoms, nitro groups and halogen atoms as a substituent(s) on a phenyl ring. The phenylsulfonyloxy groups which may have the substituent(s) are specifically exemplified by phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy and 3-chlorophenylsulfonyloxy groups. The naphthylsulfonyloxy groups are specifically exemplified by α-naphthylsulfonyloxy and β-naphthylsulfonyloxy groups.

The aralkylsulfonyloxy groups include, for example, linear or branched alkanesulfonyloxy groups having a phenyl group(s) as a substituent(s) and having 1 to 6 carbon atoms or linear or branched alkanesulfonyloxy groups having a naphthyl group(s) as a substituent(s) and having 1 to 6 carbon atoms which may have 1 to 3 groups selected from the group consisting of linear or branched alkyl groups having 1 to 6 carbon atoms, linear or branched alkoxy groups having 1 to 6 carbon atoms, nitro groups and halogen atoms as a substituent(s) on a phenyl ring. The alkanesulfonyloxy groups having a phenyl group substituted are specifically exemplified by benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy and 3-chlorobenzylsulfonyloxy groups. The alkanesulfonyloxy groups having a naphthyl group substituted are specifically exemplified by α-naphthylmethylsulfonyloxy and β-naphthylmethylsulfonyloxy groups.

A compound represented by the general formula (2) is manufactured by reacting a compound represented by the general formula (3) with a compound represented by the general formula (4).

The reaction of a compound represented by the general formula (3) with a compound represented by the general formula (4) is performed without a solvent or in an inert solvent and under the presence of a basic compound or the absence thereof.

The inert solvents include, for example, water; ether solvents such as dioxane, tetrahydrofuran, dimethyl ether, diethyl ether, diethylene glycol dimethyl ether and ethylene glycol dimethyl ether; aromatic hydrocarbon solvents such as benzene, toluene and xylene; lower alcohol solvents such as methanol, ethanol and isopropanol; ketone solvents such as acetone and methyl ethyl ketone; and polar solvents such as N,N-dimethylformamide (DMF), dimethylacetamide, dimethylsulfoxide (DMSO), hexamethylphosphoric acid triamide and acetonitrile.

As the basic compounds, a wide variety of known ones can be used, which include, for example, alkali metal hydroxides such as sodium hydroxide, potassium hydroxide, cesium hydroxide and lithium hydroxide; alkali metal carbonates such as sodium carbonate, potassium carbonate, cesium carbonate and lithium carbonate; alkali metal hydrogencarbonates such as lithium hydrogencarbonate, sodium hydrogencarbonate and potassium hydrogencarbonate; alkali metals such as sodium and potassium; inorganic bases such as sodium amide, sodium hydride and potassium hydride; alkali metal lower alkoxides such as sodium methoxide, sodium ethoxide, potassium methoxide and potassium ethoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

These basic compounds are used singly or as a mixture of two or more.

The using amount of a basic compound is usually 0.5 to 10 times mole, preferably 0.5 to 6 times mole to a compound of the general formula (3).

The above reaction may be performed, as required, by adding an alkali metal iodide such as potassium iodide or sodium iodide, as a reaction accelerator.

The ratio of the used amount of a compound of the general formula (3) to a compound of the general formula (4) in the above Reaction Formula-1 is usually 1 mole of the former to at least 0.5 mole, preferably about 0.5 to 5 mole of the latter.

The above reaction is performed usually under the temperature condition of room temperature to 200° C., preferably room temperature to 150° C., and is generally completed in about 1 to 30 hours.

The above reaction may be performed under the presence of a phase-transfer catalyst. The phase-transfer catalysts to be usable include quaternary ammonium salts (quaternary ammonium salts substituted by a group(s) selected from the group consisting of linear or branched alkyl groups having 1 to 18 carbon atoms, phenyl-substituted lower alkyl groups and phenyl groups, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, octadecyltrimethylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride and tetramethylammonium chloride); linear or branched pyridinium salts having 1 to 18 carbon atoms, such as 1-dodecanylpyridinium chloride; and phosphonium salts (phosphonium salts substituted by a linear or branched alkyl group(s) having 1 to 18 carbon atoms and/or phenyl-substituted lower alkyl groups, such as tetrabuthylphosphonium chloride). In this case, the reaction is preferably performed in water alone, or in a mixed solution with an organic solvent immiscible with water (benzene, toluene, xylene, methylene chloride, 1,2-dichloroethane, etc.).

The ratio of the used amount of a compound represented by the general formula (4) to a phase-transfer catalyst is usually one mole of the former to 0.01 to 0.5 mole, preferably 0.2 to 0.3 mole of the latter.

When the above reaction is performed under the presence of a phase-transfer catalyst, the ratio of the used amount of a compound represented by the general formula (3) to a compound represented by the general formula (4) is one mole of the former to 0.7 to 1.5 mole, preferably 0.8 to 1.0 mole of the latter.

A compound represented by the general formula (4) used as a starting raw material in the above reaction preferably has a form of lithium salt. The lithium salt of a compound represented by the general formula (4) has advantages of being stable and being easily handled. Further, the lithium salt of a compound represented by the general formula (4) is easily synthesized in a suitable solvent from a compound represented by the general formula (4) and lithium hydroxide. Therefore, the lithium salt to be used of a compound represented by the general formula (4) needs not be an isolated one, and may be one obtained by dissolving a compound represented by the general formula (4) and lithium hydroxide in water.

Compounds represented by the general formulas (3) and (4) used as starting raw materials in the reaction according to the present invention are well known.

The manufacturing method of oxazole compounds according to the present invention will be described hereinafter.

[Reaction Formula-2]

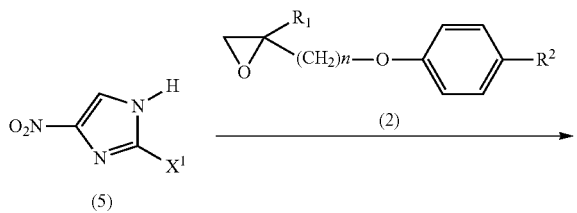

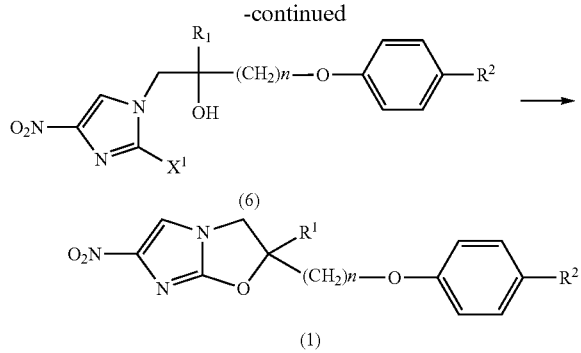

[wherein, $R^1$, $R^2$ and n are the same as the above. $X^1$ represents a halogen atom.]

According to Reaction Formula-2, a compound represented by the general formula (1) is manufactured by reacting a 4-nitroimidazole compound represented by the general formula (5) with an epoxy compound represented by the general formula (2) under the presence of a basic compound or the absence thereof to obtain a compound represented by the general formula (6), and subjecting the obtained compound represented by the general formula (6) to a ring closure reaction.

The ratio of the used amount of a compound of the general formula (5) to a compound of the general formula (2) is usually one mole of the former to 0.5 to 5 mole, preferably 0.5 to 3 mole of the former.

As the basic compounds, a wide variety of known ones can be used, which include, for example, inorganic bases such as metal hydrides, alkali metal lower alkoxides, hydroxides, carbonates and hydrogencarbonates, and organic bases such as acetates.

The metal hydrides are specifically exemplified by sodium hydride and potassium hydride.

The alkali metal lower alkoxides are specifically exemplified by sodium methoxide, sodium ethoxide and potassium tert-butoxide.

The hydroxides are specifically exemplified by sodium hydroxide and potassium hydroxide. The carbonates are specifically exemplified by sodium carbonate and potassium carbonate.

The hydrogencarbonates are specifically exemplified by sodium hydrogencarbonate and potassium hydrogencarbonate.

The inorganic bases also include sodium amides in addition to the above.

The acetates are specifically exemplified by sodium acetate and potassium acetate. The organic salts in addition to the above are specifically exemplified by triethylamine, trimethylamine, diisopropylethylamine, pyridine, dimethylaniline, 1-methylpyrrolidine, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

Such a basic compound is used usually in 0.1 to 2 mole, preferably 0.1 to 1 mole, more preferably 0.1 to 0.5 mole to one mole of a compound of the general formula (5).

The reaction of a compound of the general formula (5) and a compound of the general formula (2) is performed usually in a suitable solvent.

As the solvents, a wide variety of known ones can be used, as long as they do not inhibit the reaction, and include, for example, aprotic polar solvents such as dimethylformamide (DMF), dimethylsulfoxide (DMSO) and acetonitrile; ketone solvents such as acetone and methyl ethyl ketone; hydrocarbon solvents such as benzene, toluene, xylene, tetralin and liquid paraffin; alcoholic solvents such as methanol, ethanol, isopropanol, n-butanol and tert-butanol; ether solvents such as tetrahydrofuran (THF), dioxane, dipropyl ether, diethyl ether and diglyme; ester solvents such as ethyl acetate and methyl acetate; and mixtures thereof. These solvents may contain water.

The reaction of a compound of the general formula (5) with a compound of the general formula (2) is performed, for example, by dissolving the compound of the general formula (5) in a reaction solvent, adding a basic compound to the solution at an ice-cooling temperature to room temperature (30° C.) under stirring, stirring the mixture at room temperature to 80° C. for 30 minute to 1 hour, thereafter adding the compound of the general formula (2), and continuing stirring the mixture normally at room temperature to 100° C., preferably at 50 to 80° C. for 30 minute to 60 hours, preferably for 1 to 50 hours.

The compound (5), used as a raw material is a well-known compound. The compound of the present invention represented by the general formula (1) is manufactured by subjecting a compound represented by the general formula (6) to a ring closure reaction. The ring closure reaction is performed by dissolving the compound obtained in the above represented by the general formula (6) in a reaction solvent, and adding a basic compound thereto and stirring the mixture.

As the reaction solvents and the basic compounds, which the reaction solvents and the basic compounds used in the reaction of a compound of the general formula (5) and a compound of the general formula (2) as described above can be used.

The using amount of a basic compound is usually 1 to an excessive mole, preferably 1 to 5 mole, more preferably 1 to 2 mole to one mole of a compound of the general formula (6).

The reaction temperature of the ring closure reaction is usually at 0 to 150° C., preferably at room temperature to 120° C., more preferably at 50 to 100° C. The reaction time is usually 30 minute to 48 hours, preferably 1 to 24 hours, more preferably 1 to 12 hours.

In the present invention, the reaction mixture of a compound of the general formula (5) and a compound of the general formula (2) can be provided to the following ring closure reaction without isolating a compound of the general formula (6) produced by the reaction thereof. A target compound represented by the general formula (1) can also be manufactured, for example, by reacting a compound of the general formula (5) with a compound of the general formula (2) at room temperature to 80° C., then adding a basic compound to the reaction mixture, and further stirring the mixture at 50 to 100° C., or by reacting a compound of the general formula (5) with a compound of the general formula (2) at room temperature to 80° C., then condensing the reaction mixture, dissolving the residue in a high-boiling point solvent, adding a basic compound to the obtained solution, and further stirring the solution at 50 to 100° C.

A target compound represented by the general formula (1) can also be manufactured by using 0.9 to 2 mole of a basic compound to one mole of a compound of the general formula (5) in the reaction of the compound of the general formula (5) and a compound of the general formula (2), and stirring the reaction mixture at 50 to 100° C. to react the compound of the general formula (5) and the compound of the general formula (2) at a single process.

Compounds represented by the general formula (5) used as a starting raw material in the reaction according to the present invention are well known.

Raw material compounds used in the each reaction formula described above may be suitable salts, and target compounds obtained by the each reaction may form suitable salts. These suitable salts are those pharmacologically acceptable salts, and include salts of inorganic bases, those of organic bases, those of inorganic acids and those of organic acids.

The salts of inorganic bases include, for example, metal salts such as alkali metal salts (e.g., lithium salts, sodium salts and potassium salts) and alkaline earth metal salts (e.g. calcium salts and magnesium salts), ammonium salts, alkali metal carbonates (e.g. lithium carbonate, potassium carbonate, sodium carbonate and cesium carbonate), alkali metal hydrogencarbonates (e.g. lithium hydrogencarbonate, sodium hydrogencarbonate and potassium hydrogencarbonate), and alkali metal hydroxides (e.g. lithium hydroxide, sodium hydroxide, potassium hydroxide and cesium hydroxide).

The salts of organic bases include, for example, tri(lower)alkylamine (e.g. trimethylamine, triethylamine and N-ethyldiisopropylamine), pyridine, quinoline, piperidine, imidazole, picoline, dimethylaminopyridine, dimethylaniline, N-(lower)alkylmorpholine (e.g. N-methylmorpholine), 1,5-diazabicyclo[4.3.0]nonene-5 (DBN), 1,8-diazabicyclo[5.4.0]undecene-7 (DBU), and 1,4-diazabicyclo[2.2.2]octane (DABCO).

The salts of inorganic acids include, for example, hydrochlorides, hydrobromides, hydroiodides, sulfates, nitrates and phosphates.

The salts of organic acids include, for example, those such as formates, acetates, propionates, oxalates, malonates, succinates, fumarates, maleates, lactates, malates, citrates, tartrates, citrates, carbonates, picrates, methanesulfonates, ethanesulfonates, p-toluenesulfonates and glutamates.

Compounds having forms in which solvates (e.g. hydrates and ethanolates) are added to raw materials and target compounds indicated in the each reaction formula are included in the each general formula. Preferable solvates include hydrates.

The each target compound obtained in the above each reaction formula can be isolated and purified from a reaction mixture, for example, by separating a crude reaction product through isolation operations such as filtration, condensation and extraction after a reaction mixture is cooled, and subjecting the separated reaction product to common purification operations such as column chromatography and recrystallization.

The compounds represented by the general formula (1) according to the present invention naturally include isomers such as geometrical isomers, stereoisomers and optical isomers.

In the case where a 2,3-dihydroimidazo[2,1-b]oxazole compound represented by the general formula (1) or salts thereof, which is an active principle of tuberculostatic, is manufactured by reacting an epoxy compound or salts thereof of the present invention represented by the general formula (2) with a compound represented by the general formula (5), remarkably slight amounts of by-products are produced along with the reaction. Accordingly, using the epoxy compound of the present invention represented by the general formula (2) or salts thereof enables to manufacture a 2,3-dihydroimidazo[2,1-b]oxazole compound represented by the general formula (1) with a higher yield and a higher purity.

The epoxy compound of the present invention represented by the general formula (2) or salts thereof is a compound which is easily crystallized. Therefore, the epoxy compound of the present invention represented by the general formula (2) or salts thereof can be obtained with a high purity by a simple crystallization operation after the reaction of a compound represented by the general formula (3) or salts thereof with a compound represented by the general formula (4).

BEST MODE FOR CARRYING OUT THE INVENTION

Hereinafter, the present invention will be more clarified by way of Reference Examples and Examples.

Reference Example 1

1-ethoxycarbonyl-4-methyloxypiperidine 1-ethoxycarbonyl-4-hydroxypiperidine (30.3 g) and triethylamine (23 g) were dissolved in ethyl acetate (182 mL) and the obtained mixture was cooled to 3° C. Methanesulfonyl chloride (22.05 g) was added thereto under stirring while taking caution such that the temperature did not exceed 20° C., and the mixture was continuously stirred under ice cooling for 1 hour. The obtained reaction mixture was washed with water (90 mL×3). The organic layer was isolated and concentrated to obtain a target compound as a light yellow oily substance. The yield amount was 43.09 g (98%).

$^1$H-NMR (CDCl$_3$, 300 MHz); 1.27 (3H, t, J=7.1 Hz), 1.8-1.9 (2H, m), 1.9-2.05 (2H, m), 3.05 (3H, s), 3.3-3.45 (2H, m), 3.69-3.8 (2H, m), 4.14 (2H, q, J=7.1 Hz), 4.86-4.94 (1H, m).

Reference Example 2

1-ethoxycarbonyl-4-(4-trifluoromethoxyphenoxy)piperidine 1-ethoxycarbonyl-4-mesyloxypiperidine (13.6 g), trifluoromethoxyphenol (4.0 g), tetrabutylammonium chloride (1.2 g) and potassium carbonate (7.72 g) were suspended in water (20 mL) and the suspension was refluxed for 3 hours. The reaction solution was cooled to room temperature, and then the reaction product was extracted with toluene (24 mL). The extract was washed with water (20 mL×2), and then the solvent was concentrated under reduced pressure to obtain a target compound as a light yellow oily substance. The yield amount was 12.03 g (%). The obtained target compound was used, for the subsequent reaction without being purified.

$^1$H-NMR (CDCl$_3$, 300 Hz); 1.27 (3H, t, J=7.1 Hz), 1.7-1.8 (2H, m), 1.89-2.0 (2H, m), 3.3-3.46 (2H, m), 3.68-3.77 (2H, m), 4.14 (2H, q, J=7.1 Hz), 4.43-4.47 (1H, m), 6.89 (2H, d, J=9.1 Hz), 7.13 (2H, d, J=9.1 Hz).

Reference Example 3

4-(4-trifluoromethoxyphenoxy)piperidine

Potassium hydroxide (10.7 g) was heated to 100° C., and dissolved in isobutanol (15 mL). An isobutanol (25 mL) solution of 1-ethoxycarbonyl-4-(4-trifluoromethoxyphenoxy)piperidine (12.03 g) was dropwise added thereto while noticing generation of carbon dioxide gas. After the dropwise addition, the mixture was heated and stirred at 100° C. for 2 hours; then the solvent was concentrated; and toluene (40 mL) was added to the obtained residue. The toluene solution was washed with water (40 mL×2), and then the solvent was concentrated under reduced pressure to obtain a target compound as a light orange solid substance. The yield amount was 5.73 g (98% based on trifluoromethoxyphenol).

¹H-NMR (CDCl₃, 300 Hz); 1.59-1.71 (2H, m), 1.95-2.05 (2H, m), 2.68-2.77 (2H, m), 3.11-3.18 (2H, m), 4.29-4.37 (1H, m), 6.90 (2H, d, J=9.1 Hz), 7.13 (2H, d, J=9.1 Hz).

Reference Example 4

4-[4-(4-trifluoromethoxyphenoxy)piperidin-1-yl]phenol.paratoluenesulfonic acid salt 4-(4-trifluoromethoxyphenoxy)piperidine (4.0 g), 1,4-cyclohexanedione (2.575 g) and triethylamine (2.16 mL) were dissolved in ethanol (60 mL), and the obtained mixture was heated at 50 to 60° C., and reacted for 6 hours under air bubbling. After the reaction, the solvent was distilled off under reduced pressure; ethyl acetate (20 mL) and paratoluenesulfonic acid monohydrate (4.37 g) were added to the obtained residue; the obtained mixture was cooled, and stirred for 1 hour. The precipitated crystal was filtered, and washed with a small amount of ethyl acetate, and then dried at room temperature to obtain a target compound as a light yellow powder crystal. The yield amount was 4.465 g (55.5%).

Melting point: 211 to 214° C. (decomposing)

Purity (HPLC): 82.52%

HPLC conditions column: COSMOSIL5C8-MS (4.6φ× 250 mm); detection wavelength: 275 nm; elution condition 1: methanol/0.1M ammonium acetate aqueous solution=50/50 (40° C.); elution condition 2: methanol/0.1M ammonium acetate aqueous solution=800/200; purity=100−(the sum total of impurities detected on elution conditions 1 and 2)

¹H-NMR (DMSO-d₆ measurement temperature 70° C.); 2.05 (2H, m), 2.23 (2H, m), 2.28 (3H, s), 3.48 (2H, m), 3.59 (2H, m), 4.71 (1H, m), 6.87 (2H, m), 7.09 (2H, m), 7.13 (2H, m), 7.28 (2H, m), 7.38 (2H, m), 7.50 (2H, m) IR(KBr, cm⁻¹); 2714, 1506, 1288, 1217, 1033, 813

This compound could be further purified by recrystallizing from a mixed solution of ethyl acetate of ten-times volume and water of two-times volume, and drying at 60° C.

Form: colorless scaly crystal

Purity (HPLC): 99.8% (HPLC conditions were the same as the above)

Melting point of its pure product: 218.1 to 219.3° C. (decomposing)

Reference Example 5

4-[4-(4-trifluoromethoxyphenoxy)piperidin-1-yl]phenol

Potassium carbonate (19.3 kg) was dissolved in water (245 L), and while the obtained solution was stirred at 20 to 30° C., 4-[4-(4-trifluoromethoxyphenoxy)piperidin-1-yl]phenol.paratoluenesulfonic acid salt (49 kg) was added to the solution. The mixture was continuously stirred, for 1 hour; and then the crystal was filtered, and washed with water (245 L) (until the washing liquid exhibited neutrality). The obtained crystal was dried at about 60° C. for 42 hours. The yield amount was 31.87 kg (yield: 96.74%).

Brownish powder, Melting point: 114 to 115° C.

¹H-NMR; (300 MHz; DMSO-d₆)

1.71-1.78 (2H, m), 2.0-2.05 (2H, m), 2.81-2.89 (2H, m), 3.2-3.3 (2H, m), 4.50-4.51 (1H, m), 6.64 (2H, dd, J=3 Hz, J=9 Hz), 6.80 (2H, dd, J=3 Hz, J=9 Hz), 7.06 (2H, dd, J=3 Hz, J=9 Hz), 7.27 (2H, d, J=9 Hz), 8.82 (1H, s).

Reference Example 6

Lithium 4-[4-(4-trifluoromethoxyphenoxy)piperidin-1-yl]phenolate

4-[4-(4-trifluoromethoxyphenoxy)piperidin-1-yl]phenol.paratoluenesulfonic acid salt (105 g) and potassium carbonate (41.5 g) were added in water (525 mL), and the obtained mixture was stirred at room temperature for 2 hours. The precipitated crystal was filtered, and dissolved in isopropylalcohol (525 mL); and a solution in which lithium hydroxide monohydrate (8.0 g) was dissolved in water (45 mL) was added to the crystal solution. The obtained mixture was stirred at room temperature for 2 hours; the reaction solution was concentrated to ⅗ under reduced pressure; the residual liquid was added with toluene, and concentrated under reduced pressure till the liquid amount became about ¼. The residue was added with toluene (200 mL); and the crystal was filtered, dried at 40 to 50° C. over night to obtain a target lithium salt as a slightly brown crystal. The yield amount was 66.6 g (93%).

¹H-NMR (300 MHz, DMSO-d₆) δ; 1.6-1.8 (2H, m), 1.9-2.1 (2H, m), 2.6-2.8 (2H, m), 3.0-3.2 (2H, m), 4.3-4.5 (1H, m), 6.1-6.4 (2H, br), 6.57 (2H, d, J=8 Hz), 7.07 (2H, d, 9 Hz), 7.27 (2H, d, J=9 Hz).

Reference Example 7

Preparation of 4-[4-(Trifluoromethoxy)phenoxy]pyridine-N-oxide

4-Nitropyridine-N-oxide (84.00 g), 4-Trifluoromethoxyphenol (107.8 g), K₂CO₃ (165.7 g) and DMF (420 mL) were placed in a vessel and stirred at 80-90° C. for 4.5 hr. The reaction mixture was then cooled to room temperature and water (2500 mL) and ethyl acetate (2500 mL) were added. The organic material was taken up in ethyl acetate and then the aqueous layer was extracted with ethyl acetate (1000 mL). The all organic extracts were washed three times with water (1000 mL×3). And then the organic extracts were condensed under reduced pressure to give the crude products (150.7 g). The crude products (150.7 g) and n-hexane (1500 mL) were placed in a vessel and stirred at 60° C. for 0.5 hr and then the mixture was allowed to cool to under 10° C. for 1 hr. The mixture was then filtered and the crystalline powder washed with n-hexane (168 mL) and dried at 50° C. for 17 hr to afford 139.4 g (85.73% yield) of a brown crystal target compound.

Mp 108.5-109.5° C.

¹H-NMR (300 MHz, CDCl₃) δ=6.86-6.89 (m, 2H), 7.11-7.14 (m, 2H), 7.29-7.32 (m, 2H), 8.15-8.18 (m, 2H)

Reference Example 8

Preparation of 4-[4-(Trifluoromethoxy)phenoxy]pyridine

4-Chloropyridine hydrochloride (17.3 g), 4-Trifluoromethoxyphenol (24.6 g), K₂CO₃ (35.1 g) and DMF (173 mL) were placed in a vessel and stirred at 28-40° C. for 1.5 hr. and then stirred at 75-84° C. for 6 hr. and then stirred at 139-146° C. for 34.5 hr. The reaction mixture was then cooled to room temperature and water (256 mL), a small amount of NaCl and ethyl acetate (256 mL) were added. The organic material was taken up in ethyl acetate. The organic layer was washed with water (256 mL) and a small amount of NaCl. And then the organic layer was extracted three times with 10 v/v % HCl (256 mL×3). The organic material was taken up in 10 v/v % HCl. And then the aqueous layer was basified to pH 9 by NaOH and was extracted with ethyl acetate (256 mL). The organic material was taken up in ethyl acetate. The organic layer was washed with water (256 mL) and a small amount of NaCl. The organic layer was condensed under reduced pressure to give 15.3 g (52.0% yield) of a brown oily target compound.

$^1$H-NMR (300 MHz, CDCl$_3$) δ=6.84-6.87 (m, 2H), 7.11-7.15 (m, 2H), 7.26-7.30 (m, 2H), 8.49-8.53 (m, 2H)

Reference Example 9

Preparation of
4-[4-(Trifluoromethoxy)phenoxy]pyridine

After 4-[4-(Trifluoromethoxy)phenoxy]pyridine-N-oxide (130.0 g) was dissolved in ethanol (500 mL) and (50% wet) 5 w/w % palladium on carbon (6.5 g) was added. The resulting mixture was stirred under 3 atms of atmosphere of hydrogen at 27-49° C. for 6.5 hr. The reaction mixture was filtered to remove the catalyst followed by concentration in vacuo to give a quantitative yield (122.9 g) of pale yellow oily crude product. Purification by flash column chromatography (600 g of Silica Gel 60, spherical, ethyl acetate) afforded the pure target compound product as a colorless oil (86.74 g, 70.91% yield).

$^1$H-NMR (300 MHz, CDCl$_3$) δ=6.84-6.86 (m, 2H), 7.11-7.15 (m, 2H), 7.27-7.30 (m, 2H), 8.47-8.51 (m, 2H)

Reference Example 10

Preparation of
4-[4-(Trifluoromethoxy)phenoxy]pyridine

After 4-[4-(Trifluoromethoxy)phenoxy]pyridine-N-oxide (50 mg) was dissolved in ethanol (1.8 mL) and 10 w/w % palladium on carbon (4 mg) was added. And then Ammonium formate (120 mg) was added. The resulting mixture was stirred at 20° C. for 6 hr. The reaction mixture was filtered to remove the catalyst followed by concentration in vacuo to give a residual substance. And the a residual substance was extracted with dichloromethane. The extract was condensed under reduced pressure to give 46 mg (98% yield) of a colorless oily target compound.

$^1$H-NMR (300 MHz, CDCl$_3$) δ=6.84-6.88 (m, 2H), 7.11-7.15 (m, 2H), 7.26-7.31 (m, 2H), 8.49-8.51 (m, 2H)

Reference Example 11

Preparation of
4-[4-(Trifluoromethoxy)phenoxy]piperidine

After 4-[4-(Trifluoromethoxy)phenoxy]pyridine (2.00 g) was dissolved in acetic acid (20 mL) and platinum(IV) oxide (200 mg) was added. The resulting mixture was stirred under 4 atms of atmosphere of hydrogen at 23-30° C. for 12 hr. The reaction mixture was filtered to remove the catalyst followed by concentration in vacuo to give 3.32 g of yellow oily crude product. The crude product was dissolved in toluene (100 mL) and was washed three times with 10 w/v % NaOHaq (50 mL×3) and then was washed three times with water (50 mL×3). The organic layer was condensed under reduced pressure to give 675 mg (33.0% yield) of a pale yellow crystal target compound.

$^1$H-NMR (300 MHz, CDCl$_3$) δ=1.50-1.60 (bs, 1H), 1.60-1.68 (m, 2H), 1.98-2.03 (m, 2H), 2.68-2.76 (m, 2H), 3.10-3.18 (m, 2H), 4.28-4.36 (m, 1H), 6.83-6.92 (m, 2H), 7.09-7.15 (m, 2H)

Reference Example 12

Preparation of
4-[4-(Trifluoromethoxy)phenoxy]piperidine

After 4-(4-(Trifluoromethoxy)phenoxyl pyridine (2.00 g) was dissolved in acetic acid (20 mL) and platinum(IV) oxide (200 mg) was added. The resulting mixture was stirred under 50 atms of atmosphere of hydrogen at 24-26° C. for 7 hr 40 min. The reaction mixture was filtered to remove the catalyst followed by concentration in vacuo to give 3.89 g of colorless oily crude product. The crude product was dissolved in toluene (100 mL) and was washed three times with 10 w/v % NaOHaq (50 mL×3) and then was washed three times with water (50 mL×3). The organic layer was condensed under reduced pressure to give 772 mg (37.7% yield) of a pale yellow crystal target compound.

$^1$H-NMR (300 MHz, CDCl$_3$) δ=1.50-1.60 (bs, 1H), 1.60-1.67 (m, 2H), 1.97-2.03 (m, 2H), 2.68-2.76 (m, 2H), 3.10-3.17 (m, 2H), 4.28-4.37 (m, 1H), 6.86-6.92 (m, 2H), 7.09-7.15 (m, 2H)

Reference Example 13

Preparation of 1-(4-Benzyloxyphenyl)-4-[4-(Trifluoromethoxy)phenoxy]piperidine

4-[4-(Trifluoromethoxy)phenoxy]piperidine (26.1 g), benzyl 4-bromophenyl ether (26.3 g), palladium (II) acetate (22.4 mg), Tri-tert-butyl phosphonium tetraphenyl borate (52.3 mg), sodium tert-butoxide (10.6 g) and toluene (130 mL) were placed in a vessel and heated to reflux for 4 hr under Ar. The reaction mixture was then cooled to room temperature and water (260 mL) and ethyl acetate (260 mL) were added. The organic material was taken up in ethyl acetate. The organic layer was washed two times with water (260 mL×2). The organic layer was filtered to remove a harz and then the organic layer was condensed under reduced pressure to give 43.34 g (97.82% crude yield, 97.34% HPLC purity) of the pale yellow product. The crude product (43.3 g) and ethanol (433 mL) were placed in a vessel and heated until to dissolve and then the mixture was allowed to cool to 0° C. for 1 hr. The mixture was then filtered and the crystalline powder washed with cooled ethanol (43 mL) and then dried at 40° C. for 15 hr to afford 39.7 g (91.7% yield) of a pale yellow crystal target compound.

Total yield 89.7%
HPLC purity 100%
$^1$H-NMR (300 MHz, CDCl$_3$) δ=1.93-2.00 (m, 2H), 2.07-2.11 (m, 2H), 2.94-3.02 (m, 2H), 3.33-3.40 (m, 2H), 4.37-4.41 (m, 1H), 5.02 (s, 2H), 6.89-6.92 (m, 2H), 7.11-7.15 (m, 2H), 7.31-7.44 (m, 5H)

Reference Example 14

Preparation of 1-(4-Benzyloxyphenyl)-4-[4-(Trifluoromethoxy)phenoxy]piperidine

4-[4-(Trifluoromethoxy)phenoxy]piperidine (2.61 g), benzyl 4-bromophenyl'ether (2.63 g), palladium (II) acetate (0.67 mg), Tri-tent-butyl phosphonium tetraphenyl borate (1.57 mg), sodium tert-butoxide (1.06 g) and toluene (13 mL)

were placed in a vessel and heated to reflux for 6 hr under Ar. The reaction mixture was then cooled to room temperature and water (100 mL) and ethyl acetate (100 mL) were added. The organic material was taken up in ethyl acetate. The organic layer was washed three times with water (100 mL×3). The organic layer was filtered to remove harz and then the organic layer was condensed under reduced pressure to afford 4.36 g (98.4% yield) of a pale yellow crystal target compound.

$^1$H-NMR (300 MHz, CDCl$_3$) δ=1.93-1.99 (m, 2H), 2.07-2.11 (m, 2H), 2.93-3.01 (m, 2H), 3.32-3.39 (m, 2H), 4.38-4.40 (m, 1H), 5.02 (s, 2H), 6.89-6.91 (m, 2H), 7.11-7.15 (m, 2H), 7.30-7.41 (m, 5H)

Reference Example 15

Preparation of 1-(4-Hydroxyphenyl)-4-[4-(Trifluoromethoxy)phenoxy]piperidine

After 1-(4-Benzyloxyphenyl)-4-[4-(Trifluoromethoxy) phenoxy]piperidine (20.0 g) and ethyl alcohol (200 mL) was mixed and then (50% wet) 5 w/w % palladium on carbon (1 g) was added. The resulting mixture was stirred under 4 atms of atmosphere of hydrogen at 60-61° C. for 3 hr. The reaction mixture was then cooled to room temperature and was filtered to remove the catalyst followed by concentration in vacuo to give 16.2 g (99.5% yield) of an ivory crystal target compound.

HPLC purity 99.67%

$^1$H-NMR (300 MHz, CDCl$_3$) δ=1.93-2.00 (m, 2H), 2.08-2.13 (m, 2H), 2.93-3.01 (m, 2H), 3.30-3.38 (m, 2H), 4.38-4.43 (m, 1H), 5.1 (bs, 1H), 6.72-6.75 (m, 2H), 6.87-6.92 (m, 4H), 7.12-7.15 (m, 2H)

Reference Example 16

Synthesis of tert-butyl 4-(4-trifluoromethoxybenzyloxy)piperidin-1-carboxylate 10.00 kg of tert-butyl 4-hydroxypiperidin-1-carboxylate, 40 L of dimethoxyethane and 9.55 kg of sodium tert-butoxide were mixed, and stirred at 2 to 17° C. for 30 min. The mixture was mixed with 13.31 kg of 4-bromomethyl-1-trifluoromethoxybenzene and 10 L of dimethoxyethane at 12 to 14° C., and stirred at 21 to 23° C. for 3 hours. The reaction mixture was diluted with 100 L of water; extracted with 100 L of ethyl acetate; and the organic layer was washed with 100 L of a 1% NaCl aqueous solution twice. The organic layer was concentrated under reduced pressure to quantitatively obtain 19.21 kg of a yellow oily target substance.

Yield: 103%

$^1$H-NMR (300 MHz, CDCl$_3$) δ=1.46 (s, 9H), 1.50-1.67 (m, 2H), 1.80-1.97 (m, 2H), 3.07-3.23 (m, 2H), 3.50-3.60 (m, 1H), 3.70-3.90 (m, 2H), 4.54 (s, 2H), 7.19 (d, 2H, 8.7 Hz), 7.37 (d, 2H, 8.7 Hz)

Reference Example 17

Synthesis of 4-(4-trifluoromethoxybenzyloxy)piperidine 19.21 kg of tert-butyl 4-(4-trifluoromethoxybenzyloxy)piperidin-1-carboxylate and 50 L of ethanol were mixed, and stirred at 60° C. The mixture was mixed with 8.28 L of a concentrated hydrochloric acid, stirred at 60° C. for 2 hours, and concentrated under reduced pressure. 80 L of toluene was added to the residue; the mixture was extracted with 150 L of water; and further the water layer was washed with 40 L of toluene. 15.5 L of a 25% NaOH aqueous solution was added to the water layer; the mixture was extracted twice with 80 L and 40 L of toluene; the organic layers were combined and the organic layer was twice washed with 80 L of water; the organic layer was concentrated under reduced pressure; then, 20 L of ethanol was added to the residue; and the mixture was concentrated under reduced pressure to obtain 10.40 kg of a yellow oily target substance.

Yield: 76.04%

$^1$H-NMR (300 MHz, CDCl$_3$) δ=1.42-1.62 (m, 2H), 1.90-2.05 (m, 2H), 2.57-2.73 (m, 2H), 3.04-3.20 (m, 2H), 3.42-3.58 (m, 1H), 4.55 (s, 2H), 7.18 (d, 2H, 8.7 Hz), 7.38 (d, 2H, 8.7 Hz)

Reference Example 18

Synthesis of 1-(4-hydroxyphenyl)-4-(4-trifluoromethoxybenzyloxy)piperidine 4-methylbenzenesulfonic acid 30.0 g of 4-(4-trifluoromethoxybenzyloxy)piperidine, 18.3 g of 1,4-cyclohexanedione, 11.04 g of triethylamine and 150 mL of ethanol were mixed. After stirring at 55° C. for 7.5 hours under air-blowing (310 mL/min), the mixture was concentrated under reduced pressure. The residue was mixed with 60 mL of ethyl acetate; the mixture was concentrated under reduced pressure; 150 mL of ethyl acetate and 31.2 g of 4-methylbenzenesulfonic acid were added to the mixture; the mixture was stirred at 10° C. or less for 3 hours; then, the crystal was filtered, and dried at 60° C. over night to obtain 42.5 g of an ivory crystal target substance.

Yield: 72.3%

HPLC purity: 92.2%

$^1$H-NMR (300 MHz, DMSO-d$_6$) δ=1.70-2.40 (m, 4H), 2.29 (s, 3H), 3.30-4.10 (m, 5H), 4.61 (s, 2H), 6.88 (d, 2H, 8.6 Hz), 7.11 (d, 2H, 8.4 Hz) 7.37 (d, 2H, 7.9 Hz), 7.40-7.80 (m, 6H)

Example 1

(R)-1-[4-(2,3-epoxy-2-methylpropoxy)phenyl]-4-(4-trifluoromethoxyphenoxy)piperidine 4-[4-(4-trifluoromethoxyphenoxy)piperidine-1-yl]phenol (21.20 kg) was dissolved in acetone (164 L) under stirring, and cooled to 10° C. or less. Sodium t-butoxide (6.34 kg) was added thereto under stirring while taking caution such that the temperature of the mixed liquid did not exceed 25° C. The mixed liquid was cooled to 10° C. or less; (R)-2-methylglycidyl paranitrobenzenesulfonate (16.40 kg) was added thereto; and then the obtained mixture was heated at 40° C., and stirred for 4 hours. The reaction liquid was added with water (164 L), cooled to 10° C. or less; and the obtained mixture was stirred for 1 hour. The precipitated crystal was filtered, and washed with water (82 L). The obtained crystal was dried at about 50° C. for 20 hours to obtain a target substance as a grayish yellow crystalline powder. The yield was 23.61 kg (92.91%). This crystal was used in the subsequent reaction without being purified. A part of the crystal was recrystallized from ethanol.

Melting point: 85.8 to 86.5° C.

Purity: 89.76% HPLC), HPLC conditions column:

InertsilC8 (4.6φ×150 mm), detection wavelength: 254 nm, mobile phase composition: 0.025M phosphate buffer aqueous solution/tetrahydrofuran/acetonitrile=400/300/300, measurement temperature: 40° C.

Optical purity: 96.1% see (HPLC), HPLC conditions column: CHIRALPACK AD-H (4.6φ×250 mm), mobile phase composition: n-hexane/ethanol/diethylamine=900:100:1

$^1$H-NMR (300 MHz, CDCl$_3$) δ: 1.48 (3H, s), 1.9-2.1 (4H, m), 2.72 (1H, d, J=5 Hz), 2.86 (1H, d, J=5 Hz), 2.9-3.1 (2H, m), 3.3-3.5 (2H, m), 3.91 (1H, d, J=10 Hz), 3.98 (1H, d, J=10 JHz), 4.3-4.5 (1H, m), 6.8-7.0 (6H, m), 7.14 (2H, d, J=9 Hz).

Example 2

(R)-1-[4-(2,3-epoxy-2-methylpropoxy)phenyl]-4-(4-trifluoromethoxyphenoxy)piperidine Lithium 4-[4-(4-trifluoromethoxyphenoxy)piperidin-1-yl]phenolate (66.6 g), (R)-2-methylglycidyl paranitrobenzenesulfonate (49.1 g) and tetrabutylammonium chloride (15.5 g) were added to a mixed liquid of toluene (200 mL) and water (333 mL), and the mixture was stirred at 60° C. for 6 hours. The reaction liquid was cooled to room temperature; then the toluene layer was isolated, and washed with water; then the solvent was distilled off under reduced pressure. Isopropyl alcohol (140 mL) and water (60 mL) were added to the residue, and the obtained mixture was stirred at 60° C. for 30 min. The stirred mixture was cooled; then the precipitated crystal was filtered, and washed with a small amount of hydrated isopropyl alcohol, and dried at 50° C. over night to obtain a target substance as an orange crystal. The yield amount was 63.5 g (78%).

The crystal was recrystallized from isopropyl alcohol to obtain a colorless acicular crystal of 84 to 85° C. in melting point.

Purity: 94.6% (HPLC), HPLC conditions column: InertsilC8 (4.6φ×150 mm), detection wavelength: 254 nm, mobile phase composition: 0.025M phosphate buffer aqueous solution/tetrahydrofuran/acetonitrile=400/300/300, measurement temperature: 40° C.

Optical purity: 90% ee (HPLC), HPLC conditions column: CHIRALPACK AD-H (4.64)×250 mm), mobile phase composition: n-hexane/ethanol/diethylamine=900:100:1

$^1$H-NMR (300 MHz, CDCl$_3$) δ: 1.48 (3H, s), 1.9-2.1 (4H, m), 2.72 (1H, d, J=5 Hz), 2.86 (1H, d, J=5 Hz), 2.9-3.1 (2H, m), 3.3-3.5 (2H, m), 3.91 (1H, d, J=10 Hz), 3.98 (1H, d, J=10 JHz), 4.3-4.5 (1H, m), 6.8-7.0 (6H, m), 7.14 (2H, d, J=9 Hz).

Example 3

(R)-1-[4-(2,3-epoxy-2-methylpropoxy)phenyl]-4-(4-trifluoromethoxyphenoxy)piperidine 4-[4-(4-trifluoromethoxyphenoxy)piperidin-1-yl]phenol-.paratoluenesulfonic acid salt (5.0 g) and lithium hydroxide monohydrate (0.9 g) were added to a mixed liquid of toluene (5 mL) and water (20 mL), and the obtained mixture was stirred at 40 to 50° C. for 1 hour. The reaction liquid was cooled to 30 to 40° C.; then an aqueous solution (5 mL) of (R)-2-methylglycidyl paranitrobenzenesulfonate (2.86 g) and tetrabutylammonium chloride (0.52 g), and toluene (5 mL) were added to the reaction liquid; and the mixture was stirred at 80° C. for 2 hours. After the mixture was cooled, the toluene layer was isolated, and washed with water; and the solvent was distilled off. Methanol (25 mL) was added to the residue; the mixture was heated and dissolved; then the solution was stirred under ice cooling for about 30 to 60 min; water (10 mL) was slowly added when a crystal precipitated, and the mixture was stirred for 15 min. The precipitated crystal was filtered, and washed with a small amount of hydrated methanol, and dried at 50° C. over night to obtain a target substance as a yellow crystal. The yield amount was 3.89 g (84%).

Its purity: 83% (HPLC), HPLC conditions column: InertsilC8 (4.6φ×150 mm), detection wavelength: 254 nm, mobile phase composition: 0.025M phosphate buffer aqueous solution/tetrahydrofuran/acetonitrile=400/300/300, measurement temperature: 40° C.

Optical purity: 85% ee (HPLC), HPLC conditions column: CHIRALPACK AD-H (4.64)×250 mm), mobile phase composition: n-hexane/ethanol/diethylamine=900:100:1

$^1$H-NMR (300 MHz, CDCl$_3$) δ: 1.48 (3H, s), 1.9-2.1 (4H, m), 2.72 (1H, d, J=5 Hz), 2.86 (1H, d, J=5 Hz), 2.9-3.1 (2H, m), 3.3-3.5 (2H, m), 3.91 (1H, d, J=10 Hz), 3.98 (1H, d, J=10 JHz), 4.3-4.5 (1H, m), 6.8-7.0 (6H, m), 7.14 (2H, d, J=9 Hz).

Example 4

(R)-1-[4-(2,3-epoxy-2-methylpropoxy)phenyl]-4-(4-trifluoromethoxyphenoxy)piperidine An acetone (100 ml) solution of 4-[4-(4-trifluoromethoxyphenoxy)piperidin-1-yl]phenol (12.93 g) was cooled at 5° C., and sodium t-butoxide (3.87 g) was added thereto. The mixture, which generated heat to about 10° C., was stirred for 30 min, including a cooling time to 5° C.; and then (R)-2-methylglycidyl paranitrobenzene sulfonate (10 g) was at once added to the mixture at 5° C. The mixture was stirred at 35 to 40° C. The reaction was pursuited by HPLC, and since the reaction finally was not seen to progress, the reaction was finished at 6 hours. Water (100 mL) was added to the reaction vessel; and the reaction mixture was stirred at 10° C. or less for 30 min. The reaction mixture was filtered, and washed with water (100 mL) to obtain a target compound of 18.63 g as a wet crystal (crude yield: 120.2%). The water content was 24.4% (Karl Fisher's method). The yield was determined by the quantification by HPLC; the reduced yield was 83.50% and the HPLC purity was 86.33%.

HPLC reaction pursuiting conditions: TSK ODS-80Ts (4.6×150 mm), 20 mM Na$_2$SO$_4$ aq/CH$_3$CN/THF (3:3:3), UV 254 nm, 1 ml/min, rt.

Example 5

(R)-1-[4-(2,3-epoxypropoxy)phenyl]-4-(4-trifluoromethoxyphenoxy)piperidine

A target compound was manufactured as in Example 1, using 4-[4-(4-trifluoromethoxyphenoxy)piperidin-1-yl]phenol and (R)-glycidylnosylate as starting raw materials.

Melting point: 67.5 to 68.7° C.

$^1$H-NMR (250 MHz, CDCl$_3$) δ: 1.83-2.17 (4H, m), 2.67-2.75 (1H, m), 2.83-3.02 (3H, m), 3.25-3.40 (3H, m), 3.93 (1H, dd, J=5.6 Hz, J=11.1 Hz), 4.17 (1H, dd, J=3.3 Hz, J=11.1 Hz), 4.31-4.45 (1H, m), 6.79-6.93 (6H, m), 7.14 (2H, d, J=8.8 Hz).

Compounds of Examples 6 to 18 described below were manufactured as in Examples 1 to 5, using suitable starting raw materials.

Example 6

(R)-1-[4-(2,3-epoxy-2-methylpropoxy)phenyl]-4-(4-trifluoromethylphenoxymethyl)piperidine Melting point: 129.0 to 129.4° C.

$^1$H-NMR (250 MHz, CDCl$_3$) δ: 1.46 (3H, s), 1.51-1.70 (2H, m), 1.84-2.09 (3H, m), 2.58-2.78 (3H, m), 2.85 (1H, d,

J=4.9 Hz), 3.52 (2H, d, J=11.9 Hz), 3.79-4.03 (4H, m), 6.77-7.04 (6H, m), 7.54 (2H, d, J=8.6 Hz).

Example 7

(R)-1-[4-(2,3-epoxypropoxy)phenyl]-4-(4-trifluoromethylphenoxymethyl)piperidine

Melting Point: 131 to 131° C.
$^1$H-NMR (250 MHz, CDCl$_3$) δ: 1.45-1.64 (2H, m), 1.83-2.02 (3H, m), 2.62-2.75 (3H, m), 2.80-2.88 (1H, m), 3.26-3.43 (1H, m), 3.50-3.64 (2H, m), 3.81-3.93 (3H, m), 4.17 (1H, dd, J=3.3 Hz, J=11.0 Hz), 6.78-7.00 (6H, m), 7.54 (2H, d, J=8.7 Hz).

Example 8

(R)-1-[4-(2,3-epoxy-2-methylpropoxy)phenyl]-4-[3-(4-trifluoromethoxyphenyl)-2-propenyl]piperazine Melting point: 106.2 to 106.7° C.
$^1$H-NMR (250 MHz, CDCl$_3$) δ: 1.47 (3H, s), 2.56-2.76 (5H, m), 2.85 (1H, d, J=4.8 Hz), 3.02-3.30 (6H, m), 3.83-4.01 (2H, m), 6.18-6.36 (1H, m), 6.52 (1H, d, J=15.9 Hz), 6.79-6.94 (4H, m), 7.16 (2H, d, J=8.2 Hz), 7.33-7.46 (2H, m).

Example 9

(R)-1-[4-(2,3-epoxypropoxy)phenyl]-4-[3-(4-trifluoromethoxyphenyl)-2-propenyl]piperazine Melting point: 88.2 to 89.5° C.
$^1$H-NMR (250 MHz, CDCl$_3$) δ: 2.60-2.79 (5H, m), 2.81-2.93 (1H, m), 3.05-3.36 (7H, m), 3.92 (1H, dd, J=5.6 Hz, J=11.1 Hz), 4.16 (1H, dd, J=3.3 Hz, J=11.1 Hz), 6.82 (1H, dt, J=6.7 Hz, 15.9 Hz), 6.55 (1H, d, J=15.9 Hz), 6.81-6.93 (4H, m), 7.16 (2H, d, J=8.1 Hz), 7.40 (2H, d, J=8.1 Hz).

Example 10

(R)-4-(4-chlorobenzyloxymethyl)-1-[4-(2,3-epoxy-2-methylpropoxy)phenyl]piperidine $^1$H-NMR (250 MHz, CDCl$_3$) δ: 1.29-1.54 (5H, m), 1.63-1.98 (3H, m), 2.51-2.69 (2H, m), 2.73 (1H, d, J=4.8 Hz), 2.86 (1H, d, J=4.8 Hz), 3.34 (2H, d, J=6.3 Hz), 3.53 (2H, d, J=12.0 Hz), 3.93 (2H, dd, J=10.5 Hz, J=15.4 Hz), 4.47 (2H, s), 6.72-6.95 (4H, m), 7.18-7.37 (4H, m).

Example 11

(R)-4-(4-chlorobenzyloxymethyl)-1-[4-(2,3-epoxypropoxy)phenyl]piperidine

Melting point: 49 to 50° C. $^1$H-NMR (250 MHz, CDCl$_3$) δ: 1.29-1.50 (2H, m), 1.64-1.93 (3H, m), 2.62 (2H, dt, J=2.4 Hz, 12.0 Hz), 2.69-2.75 (1H, m), 2.82-2.90 (1H, m), 3.25-3.40 (3H, m), 3.43-3.59 (2H, m), 3.92 (1H, dd, J=5.5 Hz, J=11.0 Hz), 4.15 (1H, dd, J=3.3 Hz, J=11.0 Hz), 4.48 (2H, s), 6.79-6.93 (4H, m), 7.21-7.63 (4H, m).

Example 12

(R)-1-[4-(2,3-epoxy-2-methylpropoxy)phenyl]-4-(4-trifluoromethoxybenzyl)piperidine $^1$H-NMR (250 MHz, CDCl$_3$) δ: 1.31-1.84 (8H, m), 2.43-2.67 (4H, m), 2.72 (1H, d, J=4.8 Hz), 2.85 (1H, d, J=4.8 Hz), 3.47 (2H, d, J=12.1 Hz), 3.91 (2H, dd, J=10.5 Hz, J=15.9 Hz), 6.75-6.97 (4H, m), 7.07-7.24 (4H, m).

Example 13

(R)-1-[4-(2,3-epoxypropoxy)phenyl]-4-(4-trifluoromethoxybenzyl)piperidine

Melting point: 62.5 to 63.9° C.
$^1$H-NMR (250 MHz, CDCl$_3$) δ: 1.31-1.49 (2H, m), 1.52-1.78 (3H, m), 2.45-2.63 (4H, m), 2.67-2.76 (1H, m), 2.78-2.88 (1H, m), 3.26-3.38 (1H, m), 3.43-3.57 (2H, m), 3.92 (1H, d, J=5.5 Hz, 11.1 Hz), 4.15 (1H, d, J=3.3 Hz, 11.1 Hz), 6.76-6.90 (4H, m), 7.05-7.26 (4H, m).

Example 14

(R)-1-[4-(2,3-epoxy-2-methylpropoxy)phenyl]-4-[N-methyl-N-(4-trifluoromethoxyphenyl)]aminopiperidine Melting point: 74.0 to 74.7° C.
$^1$H-NMR (250 MHz, CDCl$_3$) δ: 1.47 (3H, s), 1.69-2.11 (4H, m), 2.61-2.90 (7H, m), 3.43-3.75 (3H, m), 3.92 (2H, dd, J=10.5 Hz, J=17.8 Hz), 6.64-6.82 (2H, m), 6.84-6.99 (4H, m), 7.01-7.17 (2H, d, J=8.5 Hz).

Example 15

(R)-4-[N-methyl-N-(4-trifluoromethoxyphenyl)]amino-1-[4-(2,3-epoxypropoxy)phenyl]piperidine Melting point: 92 to 93° C.
$^1$H-NMR (250 MHz, CDCl$_3$) δ: 1.75-2.02 (4H, m), 2.64-2.93 (7H, m), 3.26-3.40 (1H, m), 3.55-3.75 (3H, m), 3.93 (1H, dd, J=5.6 Hz, J=11.0 Hz), 4.17 (1H, dd, J=3.3 Hz, J=11.0 Hz), 6.77 (2H, d, J=8.5 Hz), 6.81-6.95 (4H, m), 7.09 (2H, d, J=8.5 Hz).

Example 16

(R)-1-(4-chlorophenyl)-4-[4-(2,3-epoxy-2-methylpropoxy)phenyl]piperazine

Melting point: 169.9 to 170.6° C.
$^1$H-NMR (250 MHz, CDCl$_3$) δ: 1.48 (3H, s), 2.73 (1H, d, J=4.8 Hz), 2.86 (1H, d, J=4.8 Hz), 3.07-3.41 (8H, m), 3.93 (2H, dd, J=10.5 Hz, J=18.9 Hz), 6.83-6.99 (6H, m), 7.14-7.32 (2H, m).

Example 17

(R)-1-(4-chlorophenyl)-4-[4-(2,3-epoxypropoxy)phenyl]piperazine

Melting point: 177.5 to 178.5° C.
$^1$H-NMR (250 MHz, CDCl$_3$) δ: 2.69-2.79 (1H, m), 2.83-2.92 (1H, m), 3.17-3.38 (9H, m), 3.94 (1H, dd, J=5.6 Hz, J=11.0 Hz), 4.18 (1H, dd, J=3.2 Hz, J=11.0 Hz), 6.81-6.98 (6H, m), 7.23 (2H, d, J=9.0 Hz).

Example 18

(R)-1-[4-(2,3-epoxy-2-methylpropoxy)phenyl]-4-(4-trifluoromethoxybenzyloxy)piperidine Melting point: 97.6 to 97.9° C.
$^1$H-NMR (250 MHz, CDCl$_3$) δ: 1.47 (3H, s), 1.71-1.93 (2H, m), 1.96-2.16 (2H, m), 2.70 (1H, d, J=4.8 Hz), 2.76-2.93

(3H, m), 3.31-3.64 (3H, m), 3.93 (2H, dd, J=10.5 Hz, J=16.5 Hz), 4.57 (2H, s), 6.75-6.96 (4H, m), 7.18 (2H, d, J=8.6 Hz), 7.39 (2H, d, J=8.6 Hz).

Example 19

(R)-2-methyl-6-nitro-2-{4-[4-(4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-(4-trifluoromethoxyphenoxy)piperidine (8.04 g), 2-bromo-4-nitroimidazole (4.53 g) and sodium acetate (387 mg) were mixed, and stirred at 110° C. for 2 hours. Dimethylformamide (20 ml) was added to the reaction liquid, and after the contents were dissolved, the reaction liquid was cooled by ice. Dimethylformamide (70 ml) was further added and the reaction liquid was cooled to −5° C. Sodium t-butoxide (2.949 g) was little by little added to the reaction liquid such that the temperature did not exceed 0° C. After about 3 hours, water (200 mL) and ethyl acetate (10 mL) were added to the reaction liquid, and stirred at 60° C. for 1 hour. The reaction liquid was cooled to 30° C., and the precipitated crystal was filtered, and washed with water (45 mL) and with methanol (20 mL). The crystal was suspended in a mixed liquid of ethyl acetate (25 mL) and methanol (25 mL), and again stirred at 60° C. for 1 hour. The suspension was cooled to 5° C., and the precipitated crystal was filtered, and then dried (at 60° C. over night) to obtain a target compound. The yield amount was 7.258 g (71.5%); and the purity was 99.49% (HPLC).

HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 99.6% ee (HPLC), HPLC conditions column: CHIRALPACK AD-H (4.64φ×250 mm), detection wavelength: 254 nm, mobile phase composition: n-hexane/ethanol/diethylamine=300/700/1

$^1$H-NMR (300 MHz, CDCl$_3$); 1.77 (3H, s), 1.8-2.2 (4H, m), 2.9-3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s).

Example 20

(R)-2-methyl-6-nitro-2-{4-[4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-(4-trifluoromethoxyphenoxy)piperidine (2.0 g) and 2-bromo-4-nitroimidazole (1.0 g) were dissolved in t-butyl acetate (2 mL); sodium acetate (77.5 mg) was added thereto; and the mixture was stirred at 95 to 100° C. for 3 hours. N,N-dimethyl acetic acid amide (18 mL) and lithium hydroxide monohydrate (238 mg) were added to the obtained solution, and the mixture was stirred at 80° C. for 4 hours. The reaction liquid was cooled, then added with water (35 mL) and stirred; and the precipitated crystal was filtered. The obtained crystal was recrystallized from a mixed liquid of methanol (20 mL) and ethyl acetate (4 mL), and dried at 60° C. over night to obtain a target substance as a light yellow crystal. The yield amount was 1.79 g (yield: 71%).

Purity: 100% (HPLC), HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 93.7% ee (HPLC), HPLC conditions column: CHIRALPACK AD-H (4.6φ×250 mm), detection wavelength: 254 nm, mobile phase composition: n-hexane/ethanol/diethylamine=300/700/1

$^1$H-NMR (300 MHz, CDCl$_3$); 1.77 (3H, s), 1.8-2.2 (4H, m), 2.9-3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s).

Example 21

(R)-2-methyl-6-nitro-2-{4-[4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-(4-trifluoromethoxyphenoxy)piperidine (2.0 g, purity: 860) and 2-bromo-4-nitroimidazole (1.0 g) were dissolved in t-butyl acetate (2 mL); sodium acetate (0.2 g) was added thereto; and the mixture was stirred at 95 to 100° C. for 3 hours. Methanol (5.5 mL) was added to the obtained solution; and then a methanol solution (2.1 mL) of 280 of sodium methylate was dropwise added to the solution at −10 to 0° C. The obtained mixture was stirred at 0° C. for 30 min; water (15 mL) was dropwise added to the mixture; and then ethyl acetate (1.1 mL) was added. Thereafter, the obtained mixture was heated at 45 to 55° C., stirred for 1 hour, and then the precipitated crystal was filtered. The obtained crystal was recrystallized from a mixed liquid of methanol (13 mL) and ethyl acetate (13 mL), and dried at 60° C. over night to obtain a target substance as a white crystal. The yield amount was 1.31 g (purity-reduced yield: 60%).

Purity: 99.7% (HPLC), HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 99.5% ee (HPLC), HPLC conditions column: CHIRALPACK AD-H (4.6φ×250 mm), detection wavelength: 254 nm, mobile phase composition: n-hexane/ethanol/diethylamine=300/700/1

$^1$H-NMR (300 MHz, CDCl$_3$); 1.77 (3H, s), 1.8-2.2 (4H, m), 2.9-3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s).

Example 22

(R)-2-methyl-6-nitro-2-{4-[4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-(4-trifluoromethoxyphenoxy)piperidine (23.66 g, purity: 86%) and 2-bromo-4-nitroimidazole (10.90 g) were dissolved in t-butyl acetate (20 mL); sodium acetate (775 mg) was added thereto; and the mixture was stirred at 95 to 100° C. for 3 hours. Methanol (60 mL) was added to the obtained solution; and then the solution was dropwise added to a solution in which sodium hydroxide (5.0 g) was dissolved in methanol (40 mL) at −10 to 0° C. The obtained mixture was stirred at 0° C. for 1 hour and 30 min; then water (100 mL) was dropwise added to the mixture; and then ethyl acetate (11 mL) was added. Thereafter, the obtained mixture was heated at 45 to 55° C., stirred for 1 hour, and then the precipitated crystal was filtered. The obtained crystal was recrystallized from a mixed liquid of methanol (160 mL) and ethyl acetate (160 mL), and dried at 60° C. over night to obtain a target substance as a light yellow crystal. The yield amount was 17.05 g (purity-reduced yield: 67.5%).

Purity: 99.9% (HPLC), HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 98.9% ee (HPLC), HPLC conditions column: CHIRALPACK AD-H (4.6φ×250 mm), detection wavelength: 254 nm, mobile phase composition: n-hexane/ethanol/diethylamine=300/700/1

1H-NMR (300 MHz, CDCl$_3$); 1.77 (3H, s), 1.8-2.2 (4H, m), 3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s).

Example 23

(R)-2-methyl-6-nitro-2-{4-[4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-(4-trifluoromethoxyphenoxy)piperidine (23.66 g, purity: 84.5%) and 2-bromo-4-nitroimidazole (10.9 g) were dissolved in t-butyl acetate (20 mL); sodium acetate (775 mg) was added thereto; and the mixture was stirred at 95 to 100° C. for 3 hours. Methanol (100 mL) was added to the obtained solution; and then a 25% sodium hydroxide aqueous solution (20.00 g) was dropwise added to the solution at −10 to 0° C. The mixture was stirred at 0° C. for 2 hours; then water (84 mL) was dropwise added to the mixture; and then ethyl acetate (11 mL) was added. Thereafter, the mixture was heated at 45 to 55° C., stirred for 1 hour, and then the precipitated crystal was filtered. The obtained crystal was recrystallized from a mixed liquid of methanol (160 mL) and ethyl acetate (160 mL), and dried at 60° C. over night to obtain a target substance as a light yellow crystal. The yield amount was 16.80 g (purity-reduced yield: 66.5%).

Purity: 99.8% (HPLC), HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 99.1% ee (HPLC), HPLC conditions column: CHIRALPACK AD-H (4.6φ×250 mm), detection wavelength: 254 nm, mobile phase composition: n-hexane/ethanol/diethylamine=300/700/1

1H-NMR (300 MHz, CDCl$_3$); 1.77 (3H, s), 1.8-2.2 (4H, m), 2.9-3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s).

Example 24

(R)-2-methyl-6-nitro-2-{4-[4-(4-trifluoromethoxyphenoxy)piperidin-1-yl]phenoxymethyl}-2,3-dihydroimidazo[2,1-b]oxazole The (R)-2-methyl-6-nitro-2-{4-[4-(4-trifluoromethoxyphenoxy)piperidin-1-yl]phenoxymethyl}-2,3-dihydroimidazo[2,1-b]oxazole, obtained in Examples 19 to 23, had a sufficiently high purity, but the purity could be further raised, for example, by the following operation.

A mixture of the (R)-2-methyl-6-nitro-2-{4-[4-(4-trifluoromethoxyphenoxy)piperidin-1-yl]phenoxymethyl}-2,3-dihydroimidazo[2,1-b]oxazole, obtained in Example 19, (7.0 g), an activated carbon (0.7 g) and acetone (70 mL) were stirred under refluxing for 30 min. The activated carbon was hot filtered, and washed with a small amount of acetone. An activated carbon (0.7 g) was added to the mother liquid, and the same operation was repeated. The mother liquid thus obtained was concentrated under reduced pressure till the mother liquid became dried. The residue was heat-dissolved in a mixed solution of ethanol (38.5 mL) and acetone (38.5 mL), then stirred at room temperature for 1 hour, and then cooled to 10° C. or less; and the precipitated crystal was filtered. The crystal was air blow-dried over night to obtain a target compound of 5.746 g (82.09%).

Purity: 99.96% (HPLC)

HPLC conditions column: ODS-0TS (4.6φ×150 mm), detection wavelength: 254 nm, mobile phase composition: 0.02M sodium sulfate/tetrahydrofuran/acetonitrile=400/300/300, measurement temperature: 40° C.

Optical purity: 99.97% ee (HPLC), HPLC conditions column: CHIRALPACK AD-H (4.6φ×250 mm), detection wavelength: 254 nm, mobile phase composition: n-hexane/ethanol/diethylamine=300/700/1

$^1$H-NMR (300 MHz, CDCl$_3$); 1.77 (3H, s), 1.8-2.2 (4H, m), 2.9-3.1 (2H, m), 3.2-3.4 (2H, m), 3.9-4.1 (2H, m), 4.02 (1H, d, J=10 Hz), 4.04 (1H, d, J=10 Hz), 4.18 (1H, d, J=10 Hz), 4.4-4.5 (1H, m), 4.50 (1H, d, J=10 Hz), 6.78 (2H, d, J=9 Hz), 6.8-7.0 (4H, m), 7.14 (2H, d, J=9 Hz), 7.56 (1H, s)

IR(KBr/cm$^{-1}$); 3133, 1609, 1513, 1340, 1038, 826

Powder X-ray (2O): 5.26°, 7.88°, 10.52°, 15.76°, 21.06°

Jet mill-crushed product (average particle diameter: 2.2 μm)

Powder X-ray (2O): 5.22°, 10.46°, 17.28°, 20.94°, 28.16°

Example 25

Synthesis of (R)-1-(4-oxiranylmethoxy)phenyl-4-(4-trifluoromethoxybenzyloxy)piperidine 31.26 kg of 1-(4-hydroxyphenyl)-4-(4-trifluoromethoxybenzyloxy)piperidine 4-methylbenzenesulfonic acid, 125 L of N,N-dimethylacetamide and 8.03 kg of potassium hydroxide were mixed, and stirred at room temperature. The mixture was mixed with 15.77 kg of (R)-oxiranylmethyl 3-nitrobenzenesulfonate, stirred at 19 to 20° C. for 2.5 hours, and cooled to 10° C. or less. The mixture was mixed with 0.904 kg of sodium dihydrogenphosphate dihydrate and 313 L of water, stirred at 50 to 60° C. for 0.5 hour; then, the crystal was filtered, washed with 156 L of water, and dried at 60° C. for 16 hours to obtain 24.06 kg of an ivory crystal target substance.

Yield: 98.09%

HPLC purity: 94.7%

Optical purity: 99.5% ee (R-isomer)

$^1$H-NMR (300 MHz, CDCl$_3$)=1.70-1.90 (m, 2H), 1.98-2.12 (m, 2H), 2.70-2.77 (m, 1H), 2.80-2.95 (m, 3H), 3.28-3.35 (m, 1H), 3.35-3.50 (m, 2H), 3.50-3.65 (m, 1H), 3.88-3.94 (m, 1H), 4.12-4.18 (m, 1H), 4.56 (s, 2H), 6.80-6.95 (m, 4H), 7.19 (d, 2H, 8.7 Hz), 7.38 (d, 2H, 8.8 Hz)

Example 26

Synthesis of (R)-1-(4-oxiranylmethoxy)phenyl-4-(4-trifluoromethoxybenzyloxy)piperidine 69.7 g of 1-(4-hydroxyphenyl)-4-(4-trifluoromethoxybenzyloxy)piperidine 4-methylbenzenesulfonic acid, 279 mL of N,N-dimethylacetamide, 17.9 g of potassium hydroxide (powder) and 31.0 g of (R)-oxiranylmethyl 4-methylbenzenesulfonate were mixed. After stirring at 15 to 21° C. for 21 hours, the mixture was mixed with 2.01 g of sodium dihydrogenphosphate dihydrate and 697 mL of water. After stirring at 35 to 45° C. for further 1 hour, the crystal was filtered, washed with 349 mL of water, and dried at 50° C. for 48 hours to obtain 53.65 g of an ivory crystal target substance.
Yield: 98.1%
HPLC purity: 97.9%
Optical purity: 84.6% ee (R-isomer)

Example 27

Synthesis of (R)-1-(4-oxiraneylmethoxy)phenyl-4-(4-trifluoromethoxybenzyloxy)piperidine 8.23 g of 1-(4-hydroxyphenyl)-4-(4-trifluoromethoxybenzyloxy)piperidine 4-methylbenzenesulfonic acid, 49.4 mL of N-methylpyrrolidone, 2.44 g of sodium hydroxide, 24.7 mL of water, 8.28 g of tetrabutylammonium hydrogensulfate and 2.82 g of (S)-epichlorohydrin were mixed. After stirring at 10° C. for 48 hours, the crystal was filtered, washed with 148 mL of cooled water, dispersed in 49 mL of cooled water, and filtered. The crystal was washed with 100 mL of cooled water, and dried at 50° C. for 18 hours to obtain 5.15 g of a target substance.
Yield: 79.8%
HPLC purity: 93.1%
Optical purity: 96.2% ee (R-isomer)

Example 28

Synthesis of a crude product of (R)-6-nitro-2-((4-(4-(4-trifluoromethoxy)benzyloxy)piperidin-1-ylphenoxy)methyl)-2,3-dihydroimidazo[2,1-b]oxazole 16.37 kg of (R)-1-(4-oxiranylmethoxy)phenyl-4-(4-trifluoromethoxybenzyloxy)piperidine, 7.42 kg of 2-bromo-4-nitro-1H-imidazole, 16 L of N,N-dimethylacetamide and 630 g of sodium acetate were mixed, and stirred at 65 to 71° C. for 8 hours; and the mixture was mixed with 131 L of N,N-dimethylacetamide. The mixture was cooled to −6° C., mixed with 3.25 kg of potassium hydroxide, and stirred at −7 to −4° C. for 6 hours. The mixture was mixed with 255 L of water and 13 L of ethyl acetate, and stirred, and then allowed to stand over night. The mixture was stirred at 35 to 38° C. for 0.5 hour, and then cooled to 24° C.; the crystal was filtered, and washed with 82 L of water to obtain 32.44 kg of a wet crystal. 32.44 kg of the wet crystal, 166 L of ethyl acetate and 158 L of methanol were mixed, and stirred and dissolved under heating and refluxing. The solution was stirred at 40 to 42° C. for 0.5 hour, and then stirred at 10 to 4° C. for 1 hour; then, the crystal was filtered, washed with a mixed liquid of 8 L of ethyl acetate and 8 L of methanol, and dried at 60° C. for 7.5 hours to obtain 7,650 g of an ocherous crystal target substance.
Yield: 37.02%
HPLC purity: 99.9%
Optical purity: 99.9% ee (R-isomer)
$^1$H-NMR (300 MHz, CDCl$_3$) δ=1.73-1.90 (m, 2H), 1.98-2.12 (m, 2H), 2.80-2.95 (m, 2H), 3.30-3.50 (m, 2H), 3.50-3.65 (m, 1H), 4.20-4.35 (m, 2H), 4.30-4.50 (m, 2H), 4.57 (s, 2H), 5.50-5.65 (m, 1H), 6.79 (d, 2H, 9.2 Hz), 6.89 (d, 2H, 9.2 Hz), 7.19 (d, 2H, 9.4 Hz), 7.38 (d, 2H, 8.7 Hz), 7.57 (s, 1H)

Example 29

Synthesis of a crude product of (R)-6-nitro-2-((4-(4-(4-trifluoromethoxy)benzyloxy)piperidin-1-ylphenoxy)methyl)-2,3-dihydroimidazo[2,1-b]oxazole 20.4 g of (R)-1-(4-oxiranylmethoxy)phenyl-4-(4-trifluoromethoxybenzyloxy)piperidine, 7.13 g of 2-chloro-4-nitro-1H-imidazole, 20.4 mL of dimethoxyethane and 3.08 g of potassium phosphate were mixed, stirred under refluxing for 2.5 hours; then, the mixture was mixed with 163.2 mL of N,N-dimethylacetoamide. The mixture was cooled to 0° C., mixed with 11.6 g of a 25% sodium hydroxide aqueous solution, and stirred at 0° C. for 2.5 hours. The mixture was mixed with 7.52 g of sodium dihydrogenphosphate dihydrate and 367 mL of water, and stirred at 35 to 40° C. for 1 hour; then, the crystal was filtered, mixed with 163 mL of methanol and 41 mL of water, and stirred at 50° C. for 0.5 hour; then, the crystal was filtered to obtain a wet crystal. The wet crystal, 153 mL of ethyl acetate and 153 mL of methanol were mixed, and stirred and dissolved under heating and refluxing. The solution was stirred at 50° C. for 1 hour, and then stirred at 0° C. for 1 hour; then the crystal was filtered, and dried at 60° C. over night to obtain 9.11 g of a target substance.
Yield: 35.4%
HPLC purity: 99.9%
Optical purity: 99.9% ee (R-isomer)

Example 30

Purification to (R)-6-nitro-2-((4-(4-(4-trifluoromethoxy)benzyloxy)piperidin-1-ylphenoxy)methyl)-2,3-dihydroimidazo[2,1-b]oxazole 7.64 kg of the crude product of (R)-6-nitro-2-((4-(4-(4-trifluoromethoxy)benzyloxy)piperidin-1-ylphenoxy)methyl)-2,3-dihydroimidazo[2,1-b]oxazole and 306 L of acetone were mixed, stirred at 15° C. for 10 min, mixed with 380 g of an activated carbon, stirred at 15° C. for 15 min, and then filtered. The filtrate was mixed with 380 g of an activated carbon and 8 L of acetone, and stirred at 15° C. for 15 min. The filtered filtrate was concentrated under ordinary pressure to distil off 237 L of acetone; then, 140 L of ethanol and 15 L of acetone were added to the residue, and the residue was dissolved under refluxing; then, the solution was stirred at 45 to 55° C. for 1 hour, stirred at 10° C. or less; then the crystal was separated, and dried at 60° C. for 18 hours to obtain 6.329 kg of a light yellow crystal target substance.
Yield: 82.820
HPLC purity: 100%
Optical purity: 99.97% ee (R-isomer)

The invention claimed is:
1. A method for manufacturing an oxazole compound or a salt thereof represented by the formula (1):

(1)

comprising reacting a compound or a salt thereof, represented by the formula (5):
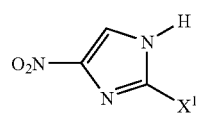
(5)
wherein X¹ represents a halogen atom, with an epoxy compound or a salt thereof, represented by the formula (2):
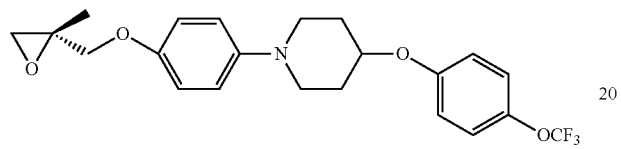
(2)
wherein the epoxy compound or a salt thereof of formula (2) is prepared by reacting a compound represented by the formula:
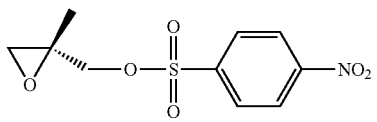 [SMILES: C[C@]1(COS(=O)(=O)c2ccc([N+](=O)[O-])cc2)CO1]
with a compound represented by the formula:
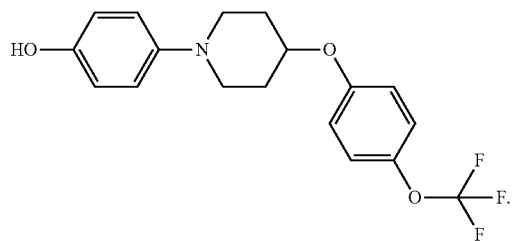 [SMILES: Oc1ccc(N2CCC(Oc3ccc(OC(F)(F)F)cc3)CC2)cc1]
* * * * *